(12) United States Patent
Moszczynski-Petkowski et al.

(10) Patent No.: US 10,138,245 B2
(45) Date of Patent: Nov. 27, 2018

(54) FUSED TRIAZOLE DERIVATIVES AS PHOSPHODIESTERASE 10A INHIBITORS

(71) Applicant: Celon Pharma S.A., Kielpin/Lomianki (PL)

(72) Inventors: Rafal Moszczynski-Petkowski, Warsaw (PL); Lukasz Bojarski, Warsaw (PL); Maciej Wieczorek, Kielpin/Lomianki (PL); Jakub Majer, Warsaw (PL); Sylwia Janowska, Inowroclaw (PL); Mikolaj Matloka, Leszno (PL); Malgorzata Borkowska, Warsaw (PL); Filip Stefaniak, Warsaw (PL); Monika Lamparska-Przybysz, Warsaw (PL); Krzysztof Dubiel, Warsaw (PL)

(73) Assignee: CELON PHARMA S.A., Kielpin/Lomianki (PL)

( * ) Notice: Subject to any disclaimer, the term of this patent is extended or adjusted under 35 U.S.C. 154(b) by 0 days.

(21) Appl. No.: 15/311,698

(22) PCT Filed: May 14, 2015

(86) PCT No.: PCT/IB2015/053549
§ 371 (c)(1),
(2) Date: Nov. 16, 2016

(87) PCT Pub. No.: WO2015/177688
PCT Pub. Date: Nov. 26, 2015

(65) Prior Publication Data
US 2017/0114064 A1   Apr. 27, 2017

(30) Foreign Application Priority Data
May 19, 2014 (PL) .......................... 408251

(51) Int. Cl.
C07D 487/04 (2006.01)
A61K 31/4985 (2006.01)
C07D 519/00 (2006.01)

(52) U.S. Cl.
CPC ........ *C07D 487/04* (2013.01); *A61K 31/4985* (2013.01); *C07D 519/00* (2013.01)

(58) Field of Classification Search
CPC . C07D 487/04; C07D 519/00; A61K 31/4985
See application file for complete search history.

(56) References Cited

FOREIGN PATENT DOCUMENTS

WO       13003298       1/2013
WO    WO2013003298   *  1/2013  ........... C07D 519/00

OTHER PUBLICATIONS

Dore et al. (European Journal of Medicinal Chemistry 84 (2014) p. 181-193).*
Sun et al. (Drug Discovery Today, v. 17, Apr. 2012, p. 310-324).*
Thomas A. Chappie et al., (2012). Current Landscape of Phosphodiesterase 10A (PDE10A) Inhibition, Journal of Medicinal Chemistry, vol. 55, No. 17, pp. 7299-7331.
Notification of Transmittal of the International Search Report and the Written Opinion of the International Searching Authority, or the Declaration, including an International Search Report and Written Opinion of the International Searching Authority, dated Jul. 28, 2015 in connection with PCT International Application No. PCT/IB2015/053549, filed May 14, 2015.

* cited by examiner

*Primary Examiner* — Robert H Havlin
(74) *Attorney, Agent, or Firm* — Gary J. Gershik; Cooper & Dunham LLP

(57) ABSTRACT

Compounds of the general formula (I), wherein one of $X_1$ and $X_2$ represents N, and the other one of $X_1$ and $X_2$ represents —C(CH$_3$), A represents unsubstituted or substituted 5-, 6- or 10-membered aryl or heteroaryl, n is 0 or 1 and B is a bicyclic heteromoiety defined in the specification. Compounds are phosphodiesterase 10A inhibitors and can find use in medicine in the treatment psychotic, neurological and cognitive functions diseases and disorders. (I)

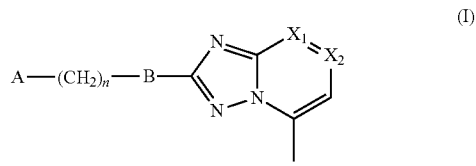

22 Claims, 2 Drawing Sheets

FUSED TRIAZOLE DERIVATIVES AS PHOSPHODIESTERASE 10A INHIBITORS

RELATED APPLICATIONS

Figure 1:
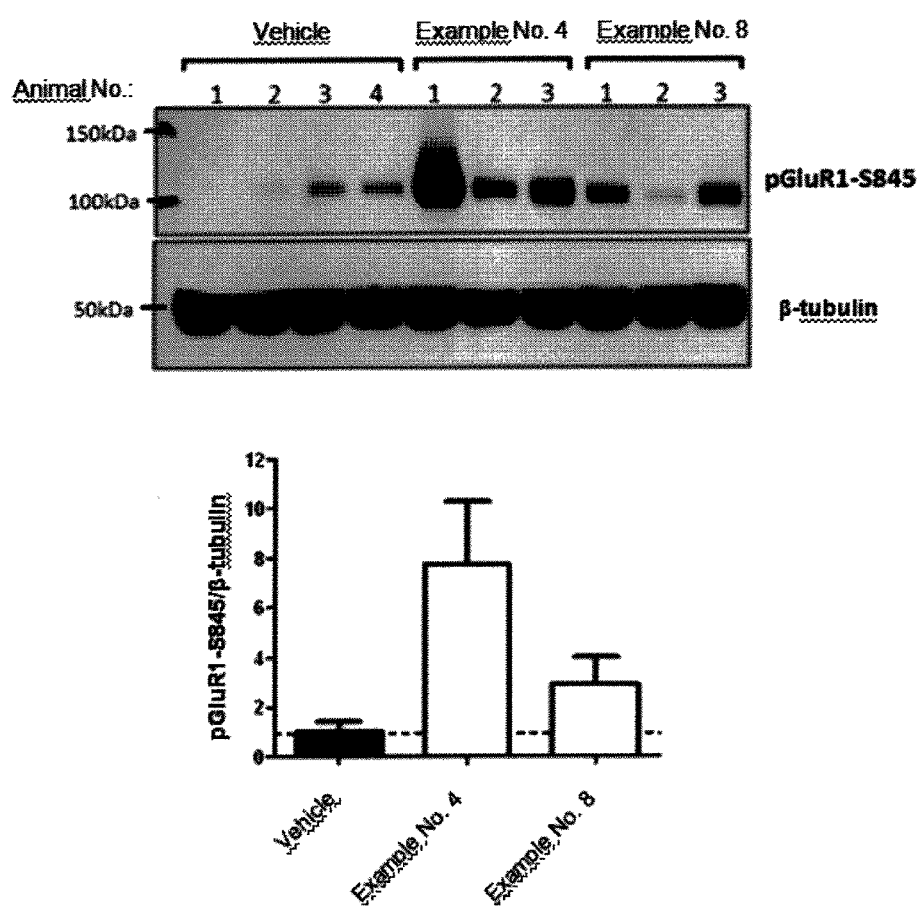

This application is a § 371 national stage of PCT International Application No. PCT International Application No. PCT/IB2015/053549, filed May 14, 2015, designating the United States, and claiming priority of Polish Patent Application No. P.408251, filed May 19, 2014, the contents of each of which are hereby incorporated by reference into this application.

TECHNICAL FIELD

The present invention relates to novel heterocyclic compounds, fused triazole derivatives that show the ability of phosphodiesterase 10A (PDE10A) inhibition, pharmaceutical compositions containing them and their use as medicaments. The compounds can find use in medicine, in particular in the treatment of psychotic diseases and disorders.

BACKGROUND ART

Phosphodiesterase 10A is an enzyme from the phosphodiesterases family with specific localisation of expression predominantly in the brain in striatum, the part of basal ganglia having various functions involved in control of motor movement, cognitive processes, emotions and learning. On the basis of presently available evidence this enzyme is believed to play a role in the regulation of response to external stimuli and in some aspects of cognitive functions. The present state of the knowledge of PDE10 activity allows to believe that compounds exhibiting the ability of PDE10A inhibition might have advantageous effects in dysfunction of basal ganglia system, including psychotic, neurological and cognitive functions disorders, such as for example psychosis, including psychosis in schizophrenia, Huntington's disease, Parkinson's disease, addictions and obsessive-compulsive disorders.

There are also reports of enhanced PDE10 expression in colorectal cancer cells. Also described is proapoptotic activity of PDE10 inhibitors against colorectal tumour-derived cell lines characterized by enhanced expression of TCF/Lef promotor-dependent genes. This allows to believe that compounds exhibiting the ability of PDE10A inhibition might have advantageous effects in the treatment of colon and rectal cancers.

In WO2013/003298 there are disclosed as phosphodiesterase 10A inhibitors the compounds based on imidazo[1,2-a]pyridine core of the following general formula, wherein X represents N or CR7, wherein R7 can be a bicyclic heteroaromatic group containing 2 to 4 nitrogen atoms.

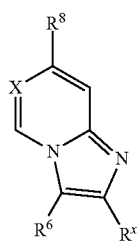

In U.S. Pat. No. 8,410,117 there are disclosed as phosphodiesterase 10A inhibitors the compounds based on carbamoyl-substituted imidazo[1,2-a]pyridine core of the following formula

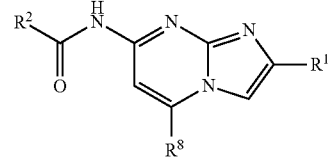

Various PDE10A inhibitors are disclosed in the art. Some of them are in the phase of clinical trials. However, none of PDE10A inhibitors has been introduced as a medicament into clinical practice.

The need still exists of search new PDE10A inhibitors of potential utility in the treatment of neurological and psychotic diseases and disorders. Such compounds are provided by the present invention.

SUMMARY OF THE INVENTION

The present invention relates to a compound of the general formula (I)

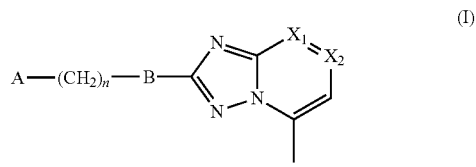

wherein:
one of $X_1$ and $X_2$ represents N, and the other one of $X_1$ and $X_2$ represents $-C(CH_3)$;
A represents an unsubstituted or substituted 5-, 6- or 10-membered aryl or heteroaryl;
B is selected from the group consisting of B1 and B2 moieties

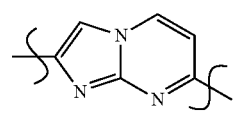

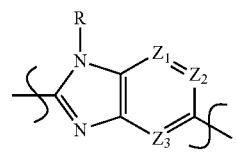

R represents H or C1-C3 alkyl;
one of $Z_1$, $Z_2$ and $Z_3$ represents $-CR^1-$, and the others of $Z_1$, $Z_2$ and $Z_3$ represent $-CH-$;
or
one of $Z_1$, $Z_2$ and $Z_3$ represents N, one of $Z_1$, $Z_2$ and $Z_3$ represents $-CH-$, and one of $Z_1$, $Z_2$ and $Z_3$ represents $-CR^1-$;
$R^1$ represents H, halogen atom, CN, or heterocycloalkyl;
n is 0 or 1;
and acid addition salts thereof.

DETAILED DESCRIPTION OF THE INVENTION

According to the invention, one of $X_1$ and $X_2$ represents N, and the other one of $X_1$ and $X_2$ represents —C(CH$_3$). That is, $X_1$ represents N and $X_2$ represents —C(CH$_3$), or alternatively $X_1$ represents —C(CH$_3$) and $X_2$ represents N.

In one variant of the moiety

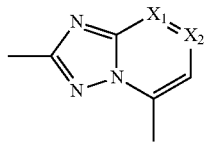

in the formula (I) of the invention, $X_1$ represents N, and $X_2$ represents —C(CH$_3$). In such a variant said moiety is a 5,7-dimethyl-[1,2,4]triazolo[1,5-a]pyrimidine moiety and is presented by formula C1

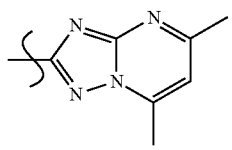

C1

In the second variant of the moiety

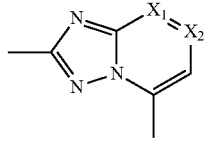

in the formula (I) of the invention, $X_1$ represents —C(CH$_3$) and $X_2$ represents N. In such a variant said moiety is a 5,8-dimethyl-[1,2,4]triazolo[1,5-a]pyrazine moiety and is presented by the formula C2

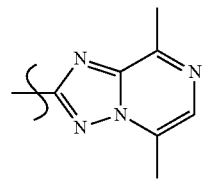

C2

Bonds indicated by curved lines in formulas of moieties B1 and B2 as well as C1 and C2 indicate places of joining of these moieties with the rest of the molecule. Said curved lines show that left sides of moieties B1 and B2 are connected with —(CH$_2$)$_n$— moiety in formula (I), while right sides of these moieties B1 and B2 are connected with bicyclic moiety

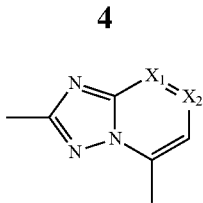

in formula (I).

In the first variant of the compounds of the invention B represents B1 moiety and in such case the compounds of the invention are represented by the formula (I1), which is specific case of the formula (I)

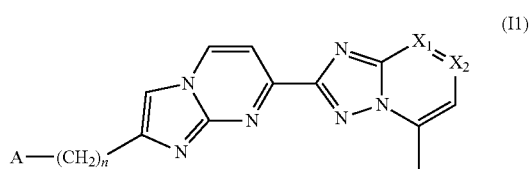

(I1)

In the second variant of the compounds of the invention B represents B2 moiety and in such case the compounds of the invention are represented by the formula (I2), which is specific case of the formula (I)

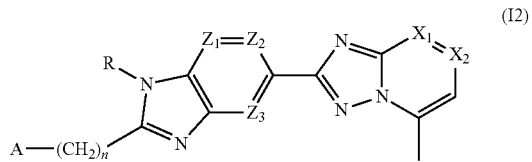

(I2)

In this second variant when B represents B2, preferably $R_1$ represents H.

One subgroup of the compounds of the invention, wherein B represents B2 moiety are those wherein one of $Z_1$, $Z_2$ and $Z_3$ represents —CR$^1$—, and the others of $Z_1$, $Z_2$ and $Z_3$ represent —CH—.

Preferably, $Z_2$ represents —CR$^1$—, and $Z_1$ and $Z_3$ both represent —CH—. In such a case B2 moiety is a benzimidazolyl moiety represented by the formula B21

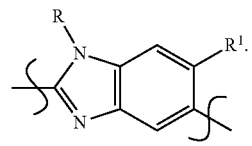

B21

In one embodiment of B21, $R_1$ represents H.

In another embodiment of B21, $R_1$ represents halogen atom, especially fluorine or bromine atom.

In yet another embodiment of B21, $R_1$ represents CN.

In yet another embodiment of B21, $R_1$ represents heterocycloalkyl, especially morpholinyl or pyrrolidinyl.

Second subgroup of the compounds of the invention, wherein B represents B2, are those wherein one of $Z_1$, $Z_2$ and $Z_3$ represents N, one of $Z_1$, $Z_2$ and $Z_3$ represents —CH—, and one of $Z_1$, $Z_2$ and $Z_3$ represents —CR$^1$—. Preferably, $R_1$ represents H.

One embodiment of the compounds of the invention of said second subgroup are those, wherein in B2 moiety $Z_1$ represents N, $Z_2$ represents —CH—, and $Z_3$ represents —CH—. In such a case B2 moiety is 3H-imidazo[4,5-b]pyridinyl, or else 4-azabenzimidazolyl, presented by the formula B22

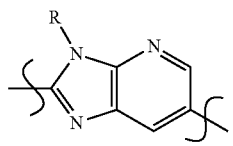

B22

Another embodiment of the compounds of the invention of said second subgroup are those, wherein in B2 moiety $Z_1$ represents —CH—, $Z_2$ represents N, and $Z_3$ represents —CH—. In such a case B2 moiety is 3H-imidazo[4,5-c]pyridinyl, or else 5-azabenzimidazolyl, presented by the formula B23

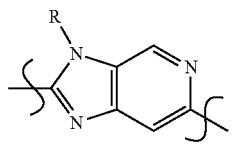

B23

Further embodiment of the compounds of the invention of said second subgroup are those, wherein in B2 moiety $Z_1$ represents —CH—, $Z_2$ represents —CH—, and $Z_3$ represents N. In such a case B2 moiety is 1H-imidazo[4,5-b]pyridinyl, or else 7-azabenzimidazolyl, presented by the formula B24

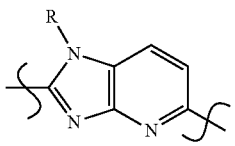

B24

Preferably, in B2, B21, B22, B23 and B24 R is H.

In another embodiment, in B2, B21, B22, B23 and B24 R is C1-C3 alkyl, especially $CH_3$.

In one of embodiments of the invention, n is 0.

In another embodiment of the invention, n is 1.

One embodiment of the compounds of the invention are the compounds of the formula (I), wherein $X_1$ represents —$C(CH_3)$, $X_2$ represents N, B represents B21, n is 0, R represents H, and $R^1$ represents H.

Further embodiment of the compounds of the invention are the compounds of the formula (I), wherein $X_1$ represents —$C(CH_3)$, $X_2$ represents N, B represents B21, n is 0, R represents H, and $R^1$ represents halogen. Halogen comprises fluorine, chlorine, bromine and iodine, especially bromine or fluorine.

Further embodiment of the compounds of the invention are the compounds of the formula (I), wherein $X_1$ represents —$C(CH_3)$, $X_2$ represents N, B represents B21, n is 0, R represents H, and $R^1$ represents CN.

Further embodiment of the compounds of the invention are the compounds of the formula (I), wherein $X_1$ represents —$C(CH_3)$, $X_2$ represents N, B represents B21, n is 0, R represents H, and $R^1$ represents heterocycloalkyl, especially morpholinyl or pyrrolidinyl.

Further embodiment of the compounds of the invention are the compounds of the formula (I), wherein $X_1$ represents —$C(CH_3)$, $X_2$ represents N, B represents B21, n is 1, R represents H, and $R^1$ represents H.

Further embodiment of the compounds of the invention are the compounds of the formula (I), wherein $X_1$ represents —$C(CH_3)$, $X_2$ represents N, B represents B1, and n is 0.

Further embodiment of the compounds of the invention are the compounds of the formula (I), wherein $X_1$ represents —$C(CH_3)$, $X_2$ represents N, B represents B1, and n is 1.

Further embodiment of the compounds of the invention are the compounds of the formula (I), wherein $X_1$ represents N, $X_2$ represents —$C(CH_3)$, B represents B1, and n is 0.

Further embodiment of the compounds of the invention are the compounds of the formula (I), wherein $X_1$ represents N, $X_2$ represents —$C(CH_3)$, B represents B1, and n is 1.

Further embodiment of the compounds of the invention are the compounds of the formula (I), wherein $X_1$ represents N, $X_2$ represents —$C(CH_3)$, B represents B21, n is 0, R represents C1-C3 alkyl, especially C1-13, and $R^1$ represents H.

Further embodiment of the compounds of the invention are the compounds of the formula (I), wherein $X_1$ represents N, $X_2$ represents —$C(CH_3)$, B represents B21, n is 0, R represents C1-C3 alkyl, especially $CH_3$, and $R^1$ represents halogen. Halogen comprises fluorine, chlorine, bromine and iodine, especially bromine or fluorine.

Further embodiment of the compounds of the invention are the compounds of the formula (I), wherein $X_1$ represents N, $X_2$ represents —$C(CH_3)$, B represents B21, n is 0, R represents C1-C3 alkyl, especially $CH_3$, and $R^1$ represents CN.

Further embodiment of the compounds of the invention are the compounds of the formula (I), wherein $X_1$ represents N, $X_2$ represents —$C(CH_3)$, B represents B21, n is 0, R represents C1-C3 alkyl, especially $CH_3$, and $R^1$ represents heterocycloalkyl, especially morpholinyl or pyrrolidinyl.

Further embodiment of the compounds of the invention are the compounds of the formula (I), wherein $X_1$ represents N, $X_2$ represents —$C(CH_3)$, B represents B22, n is 0, R represents C1-C3 alkyl, especially $CH_3$, and $R^1$ represents H.

Further embodiment of the compounds of the invention are the compounds of the formula (I), wherein $X_1$ represents N, $X_2$ represents —$C(CH_3)$, B represents B23, n is 0, R represents C1-C3 alkyl, especially $CH_3$, and $R^1$ represents H.

Further embodiment of the compounds of the invention are the compounds of the formula (I), wherein $X_1$ represents N, $X_2$ represents —$C(CH_3)$, B represents B24, n is 0, R represents C1-C3 alkyl, especially $CH_3$, and $R^1$ represents H.

Definitions of the general terms used herein are as follows.

The term 5-, 6- or 10-membered aryl or heteroaryl, which can be unsubstituted or substituted used in the definition of A comprises 6-membered aryl (i.e. phenyl), which can be unsubstituted or substituted. 5-, 6- or 10-membered heteroaryl comprises 5- and 6-membered monocyclic heteroaryls containing 1 or 2 heteroatoms selected from oxygen, nitrogen and sulphur, and 10-membered fused bicyclic heteroaryl systems, consisting of 5- or 6-membered ring and 6-membered ring, said rings containing 1 or 2 heteroatoms selected from oxygen, nitrogen and sulphur. 5-membered monocyclic heteroaryls are in particular thiazolyl, furyl, pyrazolyl, imidazolyl, isothiazolyl, oxazolyl, isoxazolyl, especially thiazolyl, furyl and pyrazolyl, 6-membered monocyclic heteroaryls are in particular pyridinyl, pyridazinyl, pyrimidinyl and pyrazinyl, especially pyridinyl and pyrimidinyl, and 10-membered heteroaryls are in particular benzothiazolyl and quinoxalinyl.

Substituents of substituted 5-, 6- or 10-membered aryl or heteroaryl are in particular halogen, especially chlorine, fluorine and bromine, C1-C4-alkyl, especially $CH_3$, CN, and —O—C1-C4-alkyl, especially —O—$CH_3$.

Halogen means fluorine (F), chlorine (Cl), bromine (Br) or iodine (I) atom.

Heterocycloalkyl in the definition of $R^1$ comprises 5- and 6-membered saturated heterocyclic rings containing 1 or 2 heteroatoms selected from oxygen, nitrogen and sulphur, such as for example pyrrolidinyl, tetrahydrofuranyl, tetrahydrothienyl, imidazolidynyl, oxazolidynyl, thiazolidynyl, dioxolanyl, dithiolanyl, oxathiolanyl, morpholinyl, piperidinyl, piperazinyl, tetrahydropyranyl and dioxanyl, especially morpholinyl and pyrrolidinyl.

Acid addition salts of the compounds of the formula (I) according to the invention comprise in particular pharmaceutically acceptable salts with inorganic or organic acids. Preferred are pharmaceutically acceptable salts. Inorganic and organic acids that are able to form pharmaceutically acceptable salts with the compounds having basic nitrogen atom and methods of their preparation are well known in the art. Salts with inorganic acids may in particular comprise salts of hydrochloric, hydrobromic, sulphuric and phosphoric acids. Salts with organic acids may in particular comprise salts of methanesulphonic, ethanesulphonic, toluenesulphonic, benzenesulphonic, naphthalenesulphonic, acetic, propionic, lactic, tartaric, malic, citric, fumaric, maleic and benzoic acids. It should be understood that the invention encompasses also salts with acids other than pharmaceutically acceptable, and that such salts may be useful in particular as intermediates in the processes of preparation, isolation and purification of the compounds of the invention.

Specific compounds of the invention are selected from the group consisting of the following compounds and acid addition salts thereof, in particular pharmaceutically acceptable acid addition salts, including inorganic and organic acids.

1) 5,7-Dimethyl-2-(2-phenyl-1H-benzo[d]imidazol-5-yl)-[1,2,4]triazolo[1,5-a]pyrimidine,
2) 2-[2-(2-Fluorophenyl)-1H-benzo[d]imidazol-5-yl]-5,8-dimethyl-[1,2,4]triazolo[1,5-a]-pyrazine,
3) 5,7-Dimethyl-2-[2-(pyridin-2-yl)-1H-benzo[d]imidazol-5-yl][1,2,4]triazolo[1,5-a]-pyrimidine,
4) 5,8-Dimethyl-2-(2-phenyl-1H-benzimidazol-5-yl)[1,2,4]triazolo[1,5-a]pyrazine,
5) 5,7-Dimethyl-2-[2-(pyridin-4-yl)-1H-benzimidazol-5-yl][1,2,4]triazolo[1,5-a]pyrimidine,
6) 2-[2-(3-Fluorophenyl)-1H-benzimidazol-5-yl]-5,8-dimethyl[1,2,4]triazolo[1,5-a]pyrazine,
7) 2-[2-(4-Fluorophenyl)-1H-benzimidazol-5-yl]-5,8-dimethyl[1,2,4]triazolo[1,5-a]pyrazine,
8) 5,8-Dimethyl-2-[2-(1,3-thiazol-2-yl)-1H-benzimidazol-5-yl][1,2,4]triazolo[1,5-a]pyrazine,
9) 2-(2-benzyl-1H-benzimidazol-5-yl)-5,8-dimethyl[1,2,4]triazolo[1,5-a]pyrazine,
10) 2-(6-Fluoro-2-phenyl-1H-benzimidazol-5-yl)-5,8-dimethyl[1,2,4]triazolo[1,5-a]pyrazine,
11) 2-[6-Fluoro-2-(pyridin-2-yl)-1H-benzimidazol-5-yl]-5,8-dimethyl[1,2,4]triazolo[1,5-a]-pyrazine,
12) 2-[5-(5,8-Dimethyl[1,2,4]triazolo[1,5-a]pyrazin-2-yl)-1H-benzimidazol-2-yl]quinoxaline,
13) 2-[2-(1,3-benzothiazol-2-yl)-1H-benzimidazol-5-yl]-5,8-dimethyl[1,2,4]triazolo[1,5-a]-pyrazine,
14) 2-[5-(5,8-Dimethyl[1,2,4]triazolo[1,5-a]pyrazin-2-yl)-1H-benzimidazol-2-yl]benzonitrile,
15) 5,8-Dimethyl-2-[2-(2-methylphenyl)-1H-benzimidazol-5-yl][1,2,4]triazolo[1,5-a]pyrazine,
16) 2-[2-(Furan-2-yl)-1H-benzimidazol-5-yl]-5,8-dimethyl[1,2,4]triazolo[1,5-a]pyrazine,
17) 5,8-Dimethyl-2-[2-(thiophen-2-yl)-1H-benzimidazol-5-yl][1,2,4]triazolo[1,5-a]pyrazine,
18) 5,8-Dimethyl-2-[2-(1,3-oxazol-4-yl)-1H-benzimidazol-5-yl][1,2,4]triazolo[1,5-a]pyrazine,
19) 5,8-Dimethyl-2-[2-(1,3-thiazol-4-yl)-1H-benzimidazol-5-yl][1,2,4]triazolo[1,5-a]pyrazine,
20) 5,8-Dimethyl-2-[2-(1,3-thiazol-5-yl)-1H-benzimidazol-5-yl][1,2,4]triazolo[1,5-a]pyrazine,
21) 2-[2-(6-Fluoropyridin-2-yl)-1H-benzimidazol-5-yl]-5,8-dimethyl[1,2,4]triazolo[1,5-a]-pyrazine,
22) 2-[2-(3-Fluoropyridin-2-yl)-1H-benzimidazol-5-yl]-5,8-dimethyl[1,2,4]triazolo[1,5-a]-pyrazine,
23) 5,8-Dimethyl-2-[2-(pyridazin-3-yl)-1H-benzimidazol-5-yl][1,2,4]triazolo[1,5-a]pyrazine,
24) 5,8-Dimethyl-2-[2-(pyrazin-2-yl)-1H-benzimidazol-5-yl][1,2,4]triazolo[1,5-a]pyrazine,
25) 5,8-Dimethyl-2-[2-(1,3-oxazol-4-yl)-1H-benzimidazol-5-yl][1,2,4]triazolo[1,5-a]pyrazine,
26) 5,8-Dimethyl-2-[2-(1,3-oxazol-2-yl)-1H-benzimidazol-5-yl][1,2,4]triazolo[1,5-a]pyrazine,
27) 5,8-Dimethyl-2-[2-(1,2-oxazol-5-yl)-1H-benzimidazol-5-yl][1,2,4]triazolo[1,5-a]pyrazine,
28) 5,8-Dimethyl-2-[2-(3-methylpyrazin-2-yl)-1H-benzimidazol-5-yl][1,2,4]triazolo[1,5-a]-pyrazine,
29) 5,8-Dimethyl-2-[2-(5-methyl-1,3-thiazol-2-yl)-1H-benzimidazol-5-yl][1,2,4]triazolo-[1,5-a]pyrazine,
30) 5,8-Dimethyl-2-[2-(4-methyl-1,3-thiazol-2-yl)-1H-benzimidazol-5-yl][1,2,4]triazolo-[1,5-a]pyrazine,
31) 5,8-Dimethyl-2-[2-(3-methyl-1,2-oxazol-5-yl)-1H-benzimidazol-5-yl][1,2,4]triazolo-[1,5-a]pyrazine,
32) 5,8-Dimethyl-2-[2-(5-methyl-1,2-oxazol-3-yl)-1H-benzimidazol-5-yl][1,2,4]triazolo-[1,5-a]pyrazine
33) 2-[2-(4-Methoxypyridin-2-yl)-1H-benzimidazol-5-yl]-5,8-dimethyl[1,2,4]triazolo[1,5-a]pyrazine,
34) 2-[2-(3-Methoxypyridin-2-yl)-1H-benzimidazol-5-yl]-5,8-dimethyl[1,2,4]triazolo[1,5-a]-pyrazine,
35) 2-[2-(3,6-Difluoropyridin-2-yl)-1H-benzimidazol-5-yl]-5,8-dimethyl[1,2,4]triazolo[1,5-a]-pyrazine,
36) 2-[2-(5-Chlorothiophen-2-yl)-1H-benzimidazol-5-yl]-5,8-dimethyl[1,2,4]triazolo[1,5-a]-pyrazine,
37) 5,8-Dimethyl-2-[2-(pyridin-3-yl)-1H-benzimidazol-5-yl][1,2,4]triazolo[1,5-a]pyrazine
38) 2-[2-(3-Bromophenyl)-1H-benzimidazol-5-yl]-5,8-dimethyl[1,2,4]triazolo[1,5-a]pyrazine,
39) 4-(4-(5-(5,8-Dimethyl[1,2,4]triazolo[1,5-a]pyrazin-2-yl)-1H-benzimidazol-2-yl)-phenyl)morpholine,
40) 5,8-Dimethyl-2-[2-(pyridin-2-yl)-1H-benzimidazol-5-yl][1,2,4]triazolo[1,5-a]pyrazine,
41) 2-[2-(2-Methoxyphenyl)-1H-benzimidazol-5-yl]-5,8-dimethyl[1,2,4]triazolo[1,5-a]-pyrazine,
42) 5,8-Dimethyl-2-[2-(1-methyl-1H-imidazol-2-yl)-1H-benzimidazol-5-yl][1,2,4]triazolo[1,5-a]pyrazine,
43) 2-(6-Bromo-2-phenyl-1H-benzimidazol-5-yl)-5,8-dimethyl[1,2,4]triazolo[1,5-a]pyrazine,
44) 5,8-Dimethyl-2-(2-phenyl-6-(pyrrolidin-1-yl)-1H-benzimidazol-5-yl)-[1,2,4]triazolo[1,5-a]pyrazine, 45) 5-(5,8-Dimethyl[1,2,4]triazolo[1,5-a]pyrazin-2-yl)-2-phenyl-1H-benzimidazolo-6-carbonitrile,
46) 4-(5-(5,8-Dimethyl-[1,2,4]triazolo[1,5-a]pyrazin-2-yl)-2-phenyl-1H-benzimidazol-6-yl)-morpholine,
47) 5,8-Dimethyl-2-(2-(3-(pyrrolidin-1-yl)phenyl)-1H-benzimidazol-[1,2,4]triazolo[1,5-a]-pyrazine,
48A) 5,7-Dimethyl-2-(1-methyl-2-phenyl-1H-benzo[d]imidazol-5-yl)-[1,2,4]triazolo[1,5-a]-pyrimidine,
48B) 5,7-Dimethyl-2-(1-methyl-2-phenyl-1H-benzo[d]imidazol-6-yl)-[1,2,4]triazolo[1,5-a]-pyrimidine,
49A) 5,7-Dimethyl-2-[1-methyl-2-(pyridin-2-yl)-1H-benzo[d]imidazol-5-yl][1,2,4]triazolo-[1,5-a]pyrimidine,
49B) 5,7-Dimethyl-2-[1-methyl-2-(pyridin-2-yl)-1H-benzo[d]imidazol-6-yl][1,2,4]triazolo-[1,5-a]pyrimidine,
50) 5,8-Dimethyl-2-(2-phenyl-3H-imidazo[4,5-c]pyridin-6-yl)[1,2,4]triazolo[1,5-a]pyrazine,
51) 5,8-Dimethyl-2-(2-phenyl-3H-imidazo[4,5-b]pyridin-6-yl)[1,2,4]triazolo[1,5-a]pyrazine,
52) 5,8-Dimethyl-2-(2-phenyl-1H-imidazo[4,5-b]pyridin-5-yl)[1,2,4]triazolo[1,5-a]pyrazine,
53) 6,8-Dimethyl-2-(2-phenyl-1H-imidazo[4,5-c]pyridin-6-yl)[1,2,4]triazolo[1,5-a]pyrazine
54) 6,8-Dimethyl-2-(2-phenyl-1H-imidazo[4,5-b]pyridin-6-yl)[1,2,4]triazolo[1,5-a]pyrazine
55) 6,8-Dimethyl-2-(2-phenyl-3H-imidazo[4,5-b]pyridin-5-yl)[1,2,4]triazolo[1,5-a]pyrazine
56) 5,7-Dimethyl-2-(2-phenylimidazo[1,2-a]pyrimidin-7-yl)[1,2,4]triazolo[1,5-a]-pyrimidine,
57) 5,8-Dimethyl-2-(2-phenylimidazo[1,2-a]pyrimidin-7-yl)[1,2,4]triazolo[1,5-a]pyrazine,
58) 5,7-Dimethyl-2-[2-(pyridin-2-yl)imidazo[1,2-a]pyrimidin-7-yl][1,2,4]triazolo[1,5-a]-pyrimidine,
59) 5,7-Dimethyl-2-[2-(1,3-thiazol-2-yl)imidazo[1,2-a]pyrimidin-7-yl][1,2,4]triazolo[1,5-a]-pyrimidine,
60) 2-[2-(2-Methoxyphenyl)imidazo[1,2-a]pyrimidin-7-yl]-5,8-dimethyl[1,2,4]triazolo[1,5-a]-pyrazine,
61) 5,8-Dimethyl-2-[2-(1,3-thiazol-2-yl)imidazo[1,2-a]pyrimidin-7-yl][1,2,4]triazolo-[1,5-a]pyrazine,
62) 5,8-Dimethyl-2-[2-(pyridin-2-yl)imidazo[1,2-a]pyrimidin-7-yl][1,2,4]triazolo[1,5-a]-pyrazine,
63) 2-[2-(5-Chlorothiophen-2-yl)imidazo[1,2-a]pyrimidin-7-yl]-5,8-dimethyl[1,2,4]triazolo-[1,5-a]pyrazine,
64) 5,8-Dimethyl-2-[2-(thiophen-2-yl)imidazo[1,2-a]pyrimidin-7-yl][1,2,4]triazolo[1,5-a]-pyrazine,
65) 2-[2-(5-Chlorothiophen-2-yl)imidazo[1,2-a]pyrimidin-7-yl]-5,8-dimethyl[1,2,4]triazolo-[1,5-a]pyrazine,
66) 2-[2-(3-Bromophenyl)imidazo[1,2-a]pyrimidin-7-yl]-5,8-dimethyl[1,2,4]triazolo[1,5-a]pyrazine,
67) 5,8-Dimethyl-2-[2-(3-(pyrrolidin-1-yl)phenyl)imidazo[1,2-a]pyrimidin-7-yl][1,2,4]-triazolo[1,5-a]pyrazine,
68) 2-(6-Bromo-2-phenylimidazo[1,2-c]pyrimidin-7-yl)-5,8-dimethyl[1,2,4]triazolo[1,5-a]pyrazine,
69) 5,8-Dimethyl-2-[2-phenyl-6-(pyrrolidin-1-yl)imidazo[1,2-a]pyrimidin-7-yl][1,2,4]-triazolo[1,5-a]pyrazine,
70) 4-[7-(5,8-Dimethyl-[1,2,4]triazolo[1,5-a]pyrazin-2-yl)-2-phenylimidazo[1,2-c]pyrimidin-6-yl]morpholine,
71) 5,8-Dimethyl-2-[6-(4-methylpiperazin-1-yl)-2-phenylimidazo[1,2-a]pyrimidin-7-yl][1,2,4]triazolo[1,5-a]pyrazine, and
72) 7-(5,8-Dimethyl[1,2,4]triazolo[1,5-a]pyrazin-2-yl)-2-phenylimidazo[1,2-a]pyrimidino-6-carbonitrile.

It has been found that the compounds of the formulae (I), (I1) and (I2) according to the invention exhibit the ability of strong inhibition of PDE10A enzyme.

The object of the invention is therefore the compound of the formula (I) as defined above for use as a medicament.

The object of the invention is also a pharmaceutical composition, comprising as an active ingredient a compound of the general formula (I) as defined above in a mixture with pharmaceutically acceptable auxiliary substances.

As PDE10A inhibitors, the compounds of the formula (I) as defined above can find use in the treatment of neurological and psychotic diseases and disorders.

The object of the invention is therefore the compound of the formula (I) as defined above for use in a method of treatment of neurological and psychotic diseases and disorders in a mammal, such as human.

The object of the invention is also the use of the compound of the formula (I) as defined above for the preparation of a medicament for the treatment of neurological and psychotic diseases and disorders in a mammal, such as human.

The object of the invention is also a method of treatment of neurological and psychotic diseases and disorders in a mammal, such as human, comprising administration of a therapeutically effective amount of the compound of the general formula (I) as defined above or the pharmaceutical composition comprising a compound of the general formula (I) as defined above.

In particular said disease or disorder is selected from the group comprising schizophrenia, delusion disorders, movement disorders, anxiety disorders, obsessive-compulsive disorders and cognitive functions disorders.

The compounds of the invention can be used for preventing, controlling or treating psychotic conditions and disorders, such as schizophrenia and delusion disorders; movement disorders such as Parkinson's disease and Huntington's disease; anxiety disorders such as panic disorder and obsessive-compulsive disorders.

Psychotic conditions and disorders that can be treated using the compounds of the invention include among others: schizophrenia (for example paranoid, hebephrenic, undifferentiated or residual type), schizophrenia-type disorders, schizoaffective disorders (delusion- or depressive type), substance-induced psychotic disorders (for example psychoses caused by alcohol, amphetamine, cannabinoids, cocaine, hallucinogens, inhaled agents, opioids, phencyclidine), hallucination disorders, paranoid personality disorder, schizoid personality disorder.

Movement disorders that can be treated using the compounds of the invention include among others: Huntington's disease, Parkinson's disease, dyskinesia induced by dopamine receptors agonists, essential tremor, restless legs syndrome (Wittmaack-Ekbom syndrome).

Anxiety disorders that can be treated using the compounds of the invention include among others: panic disorder, agoraphobia, specific (isolated) phobia types, social phobia, compulsive-obsessive disorders, acute stress disorder, posttraumatic stress disorder, generalised anxiety disorder.

Further group of disorders that can be treated using the compounds of the invention include compulsive-obsessive disorders, Tourette syndrome and other tic-involving disorders.

The compounds of the invention can be also useful in the treatment of medication- and substance-addiction syndromes, such as alcohol, amphetamine, cocaine or opiates addiction.

The compounds of the invention can be also useful in the treatment of diseases involving as one of the symptoms deficits of attention and/or cognitive functions. Examples of such diseases include among others: dementia (for example Alzheimer's disease, vascular dementia, alcohol-induced dementia, and other dementia caused by using substances, brain tumour- or head injury-associated dementia, Huntington's disease-associated dementia, AIDS-associated dementia), delirium, posttraumatic stress disorder, amnesia, intellectual disability, attention deficit hyperactivity disorder, and cognitive functions deficits in older persons.

The compounds of the invention can be also useful in the treatment of mood disorders. Examples of mood disorders include among others: mild, moderate and severe depression, manic episode and mixed episode, hypomanic episode, dysthymia, post-stroke depression, depression in schizophrenia, type I and type II bipolar affective disorder, cyclothymia.

Finally, the compounds of the invention can be also useful in the treatment of cancer, in particular colon and rectal cancer.

The compounds of the invention of the general formula (I) can be prepared as described below.

A compound of the general formula (I), wherein $X_1$=N and $X_2$=C(CH$_3$) can be obtained by reaction of iminium salt, 1-amino-4,6-dimethylpyrimidin-2(1H)-iminium diphenylphosphinate of the formula (IIA)

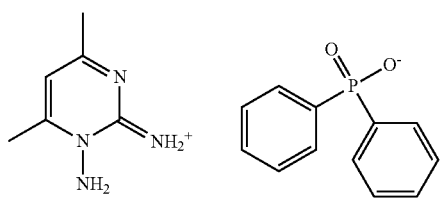

(IIA)

with an aldehyde of the general formula (III) in the case of compounds wherein B represents B1 moiety

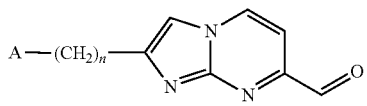

(III)

or with carboxylic acid of the general formula (IV) in the case of compounds wherein B represents B2 moiety

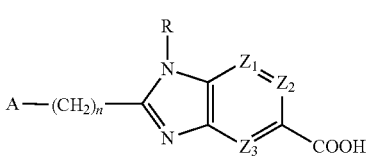

(IV)

wherein A, n, $Z_1$, $Z_2$, and $Z_3$, are as defined for formula (I).

Analogously, a compound of the general formula (I) wherein $X_1$=C(CH$_3$) and $X_2$=N can be obtained by reaction of iminium salt, 1-amino-2-imino-3,6-dimethyl-2,3-dihydro-1-pyrazinium diphenylphosphinate of the formula (IIB)

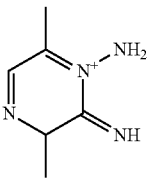 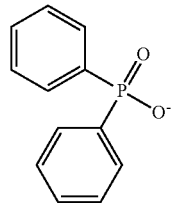

(IIB)

with an aldehyde of the general formula (III) in the case of compounds wherein B represents B1 moiety

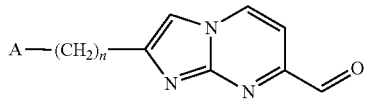

(III)

or with carboxylic acid of the general formula (IV) in the case of compounds wherein B represents B2 moiety

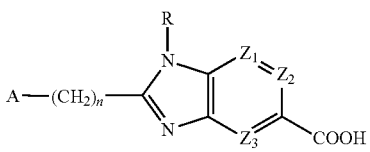

(IV)

Reaction of iminium salts (IIA) and (IIB) with aldehyde of the formula (III) or carboxylic acid of the formula (IV) can be carried out in an aprotic solvent, preferably N,N-dimethylformamide, at 80-100° C. Reaction is a two-step one. In the first step (Schiff's base formation) it is advantageous to use an inert gas atmosphere, such as argon, while in the second step (cyclisation) it is preferred to carry out the reaction under air or oxygen atmosphere.

The compound of the general formula (I), wherein B represents B2 moiety and $R^1$ represents C1-C3 alkyl, can be prepared by alkylation of the corresponding compound of the general formula (I) wherein B represents B2 moiety and $R^1$ is hydrogen.

Alkylation can be carried out in a manner known in the art using any known alkylating agent. Preferred alkylating agent is C1-C3 alkyl halogenide, such C1-C3 alkyl bromide, chloride or iodide, preferably C1-C3 alkyl iodide.

Aldehyde of the formula (III) as defined above can be prepared by condensation of bromoketone of the formula (V), wherein A and n are as defined for formula (I), with aminopyrimidine of the formula (VI)

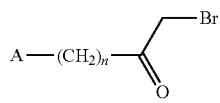

(V)

(VI)

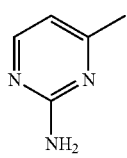

to obtain imidazopyrimidine of the formula (VII), wherein A and n are as defined for formula (I)

(VII)

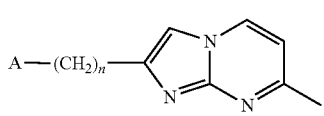

Condensation can be carried out in the presence of an inorganic base, such as potassium carbonate, caesium carbonate or sodium hydroxide, or an organic base such as triethylamine or N,N-diisopropylethylamine (DIPEA), at reflux of the solvent. The solvent can be an alcohol, such as methanol, ethanol, especially ethanol, or aprotic solvent such as diglyme, acetone, dichloromethane or N,N-dimethylformamide.

Imidazopyrimidine of the formula (VII) is subsequently converted to enamine of the formula (VIII), wherein A and n are as defined for formula (I)

(VIII)

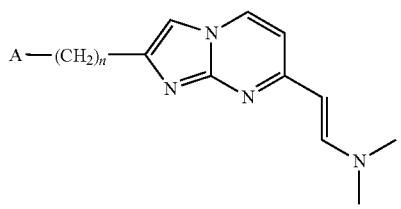

by reaction with N,N-dimethylformamide dimethyl acetal (DMA) carried out in N,N-dimethylformamide at elevated temperature, typically 140° C. In order to enhance the yields of the products the reaction can be carried out in a pressure vessel, such as closed tube or autoclave.

Finally, enamine derivative of the formula (VIII) is converted to an aldehyde of the formula (II) by reaction with sodium periodate.

Reaction with sodium periodate is carried out in the temperature range of 0-20° C. in a solvent. Wide range of solvents, such as water, tetrahydrofuran, methanol, or dichloromethane, can be used. Tetrahydrofuran is a preferred solvent.

Carboxylic acid of the above formula (IV), wherein $Z_1$, $Z_2$, $Z_3$, A and n are as defined for the formula (I), can be prepared from an aldehyde of the formula (IX) or an acid of the formula (X), wherein A and n are as defined for the formula (I)

(IX)

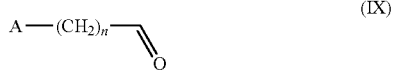

(X)

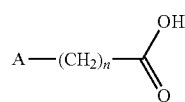

in condensation reaction with diamine of the formula (XI)

(XI)

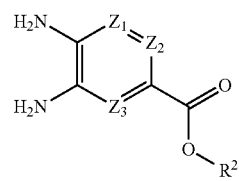

wherein $R^2$ represents methyl or ethyl group, and $Z_1$, $Z_2$, and $Z_3$ are as defined for the formula (I), to obtain an ester of the formula (XII), wherein $R^2$ represents methyl or ethyl group, and $Z_1$, $Z_2$, $Z_3$, A and n are as defined for the formula (I)

(XII)

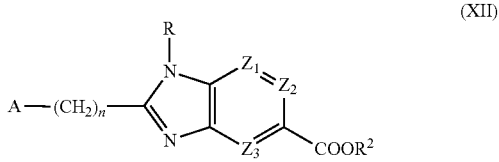

which is converted in an acid of the formula (IV) by hydrolysis using known methods.

Condensation of the aldehyde of the formula (IX) with diamine of the formula (XI) is carried out at elevated temperature (usually at reflux of the solvent), using equimolar amounts of the reagents. Wide range of solvents can be used (protic solvents, for example methanol, water, ethanol, polyethylene glycol; aprotic solvents, for example nitrobenzene, acetonitrile, N,N-dimethylformamide, toluene, 1,4-dioxane). Better results can be obtained by carrying out the reaction under oxygen atmosphere in the presence of, for example, iron (III) oxide or sodium pyrosulfite in an aprotic solvent (for example acetonitrile or DMF). Hydrogen peroxide or ammonium cerium (IV) nitrate can be also used as oxidizing agent. The reaction can be also carried out in an acidic environment (for example in acetic acid, using microwave radiation, or using hydrogen chloride in methanol/water or water/acetonitrile system).

Condensation of the acid of the formula (IX) with diamine of the formula (XI) can be carried out without solvent at elevated temperature (100-170° C.), under acidic conditions (polyphosphoric acid, acetic acid, hydrogen chloride, phosphorus oxychloride). If the reaction is carried out in a solvent, protic solvents (water, methanol, ethanol, polyethylene glycol) and aprotic solvents (N,N-dimethylformamide, dichloromethane, tetrahydrofuran (THF), benzene, ethyl acetate) can be used. Commonly known in the art is the method with the use of a coupling agent, such as 1-(3-dimethylaminopropyl)-3-ethylcarbodimide hydrochloride (EDCI) or 1-[bis(dimethylamino)methylene-1H-1,2,3-triazolo[4,5-b]pyridinium hexafluorophosphate (HATU), with Hunig's base (N,N-diisopropylethylamine) (the reactions run in DMF or THF). Condensation can also run in water in the presence of a catalyst (for example Amberlyst-15) and microwave radiation.

Diamines of the formula (XI), in the case when one of $Z_1$, $Z_2$ and $Z_3$ represents —CH—, and the others represent —$CR^1$—, are commercially available. Diamines of the formula (XI), in the case when $Z_1$ or $Z_2$ represents N, can be also prepared in a manner known in the art from corresponding 4- or 5-monoamine derivative of nicotinic or picolinic acid, respectively, by the following steps, in succession: nitration, for example with potassium nitrate in the presence of sulphuric acid, esterification with alcohol, and reduction of nitro group by hydrogenation. Diamines of the formula (XI), in the case when $Z_3$ represents N, can be prepared from 6-amino-5-nitro-2-picoline by reaction with N,N-dimethylformamide dimethyl acetal (DMA), subsequent oxidation, esterification and finally reduction of nitro group by hydrogenation. Preparation of diamines of the formula (XI) is illustrated in more details in the Examples.

The compounds of the formula (I) can be administered in the treatment in the form of a pharmaceutical composition or preparation containing them.

In the treatment of disorders, diseases, and conditions mentioned above the compounds of the formula (I) of the invention can be administered as a chemical compound, however usually will be used in the form of a pharmaceutical composition comprising the compound of the invention or its pharmaceutically acceptable salt in combination with pharmaceutically acceptable carrier(s) and auxiliary substance(s).

In the treatment of disorders, diseases, and conditions mentioned above the pharmaceutical composition of the invention can be administered by any suitable route, preferably oral, parenteral or inhalation route and will be in the form of a preparation destined for use in medicine, depending on the intended administration route.

Compositions for oral administration can have the form of solid or liquid preparations. Solid preparations can have, for example, the form of a tablet or capsule produced in a conventional manner from pharmaceutically acceptable inactive excipients such as binders (for example, pregelatinised corn starch, polyvinylpyrrolidone or hydroxypropylmethylcellulose); fillers (for example lactose, saccharose, carboxymethylcellulose, microcrystalline cellulose or calcium hydrogenphosphate); disintegrants (for example crosspovidone, corn starch or sodium starch glycolate); lubricants (for example magnesium stearate, talc or silica), wetting agents (for example sodium laurylsulphate). Tablets can be coated with coatings well known in the art, such as simple coatings, delayed/controlled-release coatings or enteric coatings. Liquid preparations for oral administration can be in a form of, for example, solutions, syrups or suspensions, or can have the form of dry solid product for reconstitution in water or other suitable vehiculum before use. Such liquid preparations can be prepared using conventional means from pharmaceutically acceptable inactive excipients, such as suspending agents (for example sorbitol syrup, cellulose derivatives or hydrogenated edible oils), emulsifiers (for example lecithine or acacia gum), nonaqueous vehicles (for example mandelic oil, oil esters, ethyl alcohol or fractionated vegetable oils), and preservatives (for example methyl or propyl p-hydroxybenzoate or sorbic acid). Preparations can also include suitable buffering agents, flavoring agents, coloring agents and sweeteners.

Preparations for oral administration can be formulated so as to obtain controlled release of the active compound using methods known for a person skilled in the art.

Parenteral route of administration includes administration by intramuscular and intravenous injections, as well as intravenous infusions. Compositions for parenteral administration can, for example, have the form of a unit dosage form, such as ampoules, or multi-dosage containers, with the addition of a preservative. Compositions can have the form such as suspension, solution or emulsion in an oily or aqueous vehiculum, and can include excipients such as suspending agents, stabilizers, and/or dispersing agents. Alternatively, the active ingredient can be formulated as a powder for reconstitution before use in a suitable carrier, for example sterile, pyrogen-free water.

Compositions for administration via inhalation route can have the inhalation form and administered by nebulization. Such preparations include an active compound and auxiliary substance(s) administered as an aerosol, i.e. a system of finely divided small particles of solid or liquid substance suspended in a gas. Auxiliary substances used in nebulization can be for example sodium chloride as an isotonicity agent, inorganic acids and hydroxides as pH regulators and stabilisers, benzalkonium chloride as a preservative, sodium citrate as a buffering agent, polysorbate 80 as a surfactant, ethanol and propylene glycol as a co-solvent, and sulphates (VI) as anti-oxidants. Preparations for administration by inhalation route can have the form of pressure inhalers or dry powder inhalers.

The method of treatment with the use of the compounds of the present invention will comprise administration of a therapeutically effective amount of the compound of the invention, preferably in the form of a pharmaceutical composition, to the subject in need of such treatment.

Proposed dosage of the compounds of the invention is from 0.1 to about 1000 mg per day, in a single dose or in divided doses. It will be apparent for a person skilled in the art that selection of a dosage required for obtaining desirable biological effect will depend on many factors, for example specific compound, the indication, the manner of administration, the age and condition of a patient and that exact dosage will be ultimately determined by a responsible physician.

EXAMPLES

Intermediates

In the following Examples generally known methods of synthesis of Intermediates used for the preparation of the compounds of the invention are set forth. The Examples are solely illustrative.

Iminium Salts (IIA) and (IIB)

1-Amino-4,6-dimethylpyrimidin-2(1H)-iminium diphenylphosphinate (IIA)

The solution of 2-amino-4,6-dimethylpyrimidine (4.18 g, 34.0 mmol) in dry dichloromethane (80 mL) was put under argon and cooled in an ice-bath to 0° C. Then to the solution 8.8 g (34.0 mmol) of O-(diphenylphosphinyl)hydroxylamine were added portionwise. The resulted white suspension was stirred for 24 hours, then the mixture was slowly brought to room temperature (without removing the ice-bath). White solid product thus formed was filtered on Schott funnel. The filtrate was concentrated, obtained yellow solid was triturated with dichloromethane and filtered-off (second crop). Combined solids were dried under reduced pressure to obtain 7.78 g of the title product (yield 64%). MS-ESI: (m/z) calculated for $C_6H_{10}N_4$ [M+H]$^+$: 139.09, found 139.1 (iminium cation); calculated for $C_{12}H_{11}O_2P$ [M−H]$^-$: 217.04, found 217.1 (diphenylphosphinate anion).

1-Amino-2-imino-3,6-dimethyl-2,3-dihydro-1-pyrazinium diphenylphosphinate (IIB)

In a pressure tube were placed 4 mL of 25% ammonia solution, 64 mg of powdered copper and 1.0 g (6.66 mmol) of 3-chloro-2,5-dimethylpyrazine. The whole was heated to 150° C. for 18 hours. Further 1 mL of 25% ammonia solution was added and heating was continued for further 4 hours. The mixture was filtered through silica gel layer, washed with 10 mL of water and 10 mL of ethyl acetate. The filtrate was extracted with ethyl acetate (5×10 mL). Organic phase was dried over sodium sulphate and concentrated. Resulted solid was triturated with heptane and filtered-off (first crop). Second crop of the product crystallized from the filtrate. Combined solids were dried under reduced pressure to obtain 0.60 g of 2-amino-3,6-dimethylpyrazine as a solid (yield 73%). $^1$H NMR (300 MHz, DMSO-$d_6$): δ 7.45 (s, 1H), 6.01 (s, broad, 2H), 2.22 (s, 3H), 2.10 (s, 3H).

To the solution of thus obtained 2-amino-3,6-dimethyl-pyrazine (4.0 g, 32.5 mmol) in dry dichloromethane (150 mL), 6.89 g (29.5 mmol) of O-(diphenylphosphinyl)hydroxylamine were added at room temperature. The whole was stirred at room temperature for 20 hours. The mixture was concentrated to the constant mass and after addition of isopropanol (50 mL)-toluene (10 mL) mixture concentrated again to remove traces of water. Dry residue was triturated with ethyl ether. Obtained solid was filtered-off and dried under reduced pressure. 6.91 g of the title product as a brown solid were obtained (yield 66%). MS-ESI: (m/z) calculated for $C_6H_{10}N_4$ [M+H]$^-$: 139.09, found 139.1 (pyrazinium cation); calculated for $C_{12}H_{11}O_2P$ [M−H]$^-$: 217.04, found 217.1 (diphenylphosphinate anion).

Intermediate VII. 7-Methyl-2-phenylimidazo[1,2-a]pyrimidine

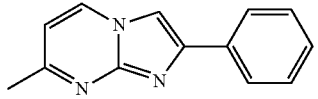 [SMILES: Cc1ccn2cc(-c3ccccc3)nc2n1]

To the suspension of 2-bromo-1-phenylethanone (5.31 g, 26.7 mmol) in absolute ethanol (50 mL) solid 2-amino-4-methylpyrimidine (3.0 g, 26.7 mmol) was added during several minutes.

The whole was heated at reflux for 5 hours (after heating both starting materials dissolved). To the mixture were added 200 mL of chloroform and 100 mL of water. Aqueous phase was neutralized with 6M aqueous sodium hydroxide solution, brought to pH=9 with saturated sodium hydrogen carbonate solution and extracted with chloroform (3×40 mL). Extracts were dried over sodium sulphate and concentrated. Obtained raw product was crystallized from ethyl acetate/ethanol (2:1). 3.92 g of the title product were obtained (yield 71%). $^1$H NMR (300 MHz, CDCl$_3$): δ 9.18 (d, 1H), 8.69 (s, 1H), 8.00-7.98 (dd, 2H), 7.62-7.54 (m, 4H), 2.51 (s, 3H).

Intermediate VIII. (E)-N,N-dimethyl-2-(2-phenylimidazo[1,2-a]pyrimidin-7-yl)ethenamine

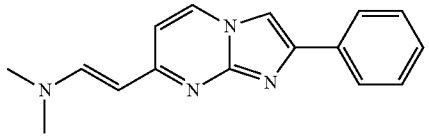 [SMILES: CN(C)/C=C/c1ccn2cc(-c3ccccc3)nc2n1]

To the solution of 7-methyl-2-phenylimidazo[1,2-a]pyrimidine (Intermediate VII, 0.20 g, 0.96 mmol) in dry N,N-dimethylformamide the solution of N,N-dimethylformamide dimethyl acetal (DMA) in N,N-dimethylformamide (1:1, 1.4 mL, 10.5 mmol) was added dropwise and the whole was heated under argon atmosphere at 90° C. for 5 hours. The solvent was removed under reduced pressure, the residue was purified by chromatography on silicagel (ethyl acetate as eluent). 0.12 g of the title product (yield 47%) were obtained as a solid. MS-ESI: (m/z) calculated for $C_{16}H_{16}N_4$ [M+H]$^+$: 265.14, found 265.1.

Intermediates III—Aldehydes of the Formula (III)

Intermediate III-1. 2-Phenyl imidazol-[1,2-a]pyrimidino-7-carboxyaldehyde

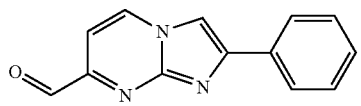 [SMILES: O=Cc1ccn2cc(-c3ccccc3)nc2n1]

To the solution of (E)-N,N-dimethyl-2-(2-phenylimidazo[1,2-a]pyrimidin-7-yl)etheneamine (Intermediate VIII, 0.11 g, 0.42 mmol) in tetrahydrofuran at 0° C. under argon atmosphere sodium periodate (0.27 g, 1.25 mmol) was added. After addition of sodium periodate the whole was heated to room temperature and stirred for 4 hours. To the mixture of 50 mL chloroform with methanol (3 mL) were added and the whole was filtered-off through celite. The filtrate was concentrated and the residue purified by chromatography on silicagel (eluent: chloroform-methanol, gradient 0-2%). 50 mg of the title product were obtained (yield 54%). MS-ESI: (m/z) calculated for $C_{13}H_9N_3ONa$ [M+Na]$^+$: 246.21, found 246.1.

Intermediates III set forth in Table 1 were obtained from suitable starting materials analogously as Intermediate III-1 and used for the preparation of the compounds of the invention.

TABLE 1

| Intermediate III | A | n | B-CHO | MS-ESI [M + Na]$^+$ |
|---|---|---|---|---|
| III-2 | | 0 | | 246.1 |

TABLE 1-continued

| Intermediate III | A | n | B-CHO | MS-ESI [M + Na]+ |
|---|---|---|---|---|
| III-3 | 2-methylpyridine | 0 | imidazo[1,2-a]pyrimidine-carbaldehyde | 247.1 |
| III-4 | 2-methylthiazole | 0 | imidazo[1,2-a]pyrimidine-carbaldehyde | 253.1 |
| III-5 | 2-methyl-anisole | 0 | imidazo[1,2-a]pyrimidine-carbaldehyde | 276.1 |
| III-6 | 5-chloro-2-methylthiophene | 0 | imidazo[1,2-a]pyrimidine-carbaldehyde | 286.7 |

Intermediates XII—Benzimidazole Esters

Intermediate XII-1. Ethyl 2-phenyl-1H-benzimidazole-5-carboxylate

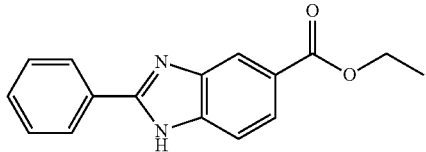 [SMILES: CCOC(=O)c1ccc2[nH]c(-c3ccccc3)nc2c1]

The mixture of 5.00 g (27.7 mmol) of ethyl 3,4-diaminobenzoate, 3.32 g (27.7 mmol) of benzoic acid and 20 mL of polyphosphoric acid was heated at 140° C. for 3 hours. Warm reaction mixture was poured onto ice covered with solid sodium hydrogen carbonate and then 60 mL of ethyl acetate were added. Aqueous phase was extracted with ethyl acetate (4×70 mL). Extracts were dried over sodium sulphate and concentrated. The raw product was purified by chromatography on silicagel (eluent: heptane/ethyl acetate, 40/60). 3.14 g of the title product as a solid were obtained (yield 43%). $^1$H NMR (300 MHz, CDCl$_3$): δ 8.37 (s, 1H), 8.13-8.11 (m, 2H), 7.99 (d, 2H), 7.64 (d, 2H), 7.45-7.43 (m, 2H), 4.42 (q, 2H), 1.40 (t, 3H). MS-ESI: (m/z) calculated for C$_{16}$H$_{14}$N$_2$O$_2$ [M+H]$^+$: 267.1, found 267.1.

Intermediate XII-2. Ethyl 2-(2-fluorophenyl)-1H-benzimidazole-5-carboxylate

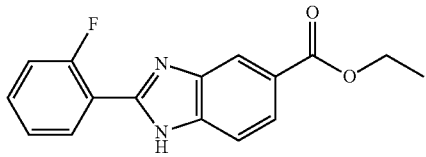 [SMILES: CCOC(=O)c1ccc2[nH]c(-c3ccccc3F)nc2c1]

To the solution of ethyl 3,4-diaminobenzoate (1.06 g, 5.76 mmol) in dry N,N-dimethylformamide (25 mL) 2-fluorobenzaldehyde (1.61 g, 12.70 mmol) was added and the mixture was stirred for 5 minutes. To the resulted mixture solid sodium pyrosulfite (2.41 g, 12.7 mmol) was added and the whole was stirred at room temperature for 20 hours. The solvent was removed under reduced pressure and 100 mL of water and 50 mL of ethyl acetate were added to the residue. Aqueous phase was separated and extracted with ethyl acetate (5×30 mL). Extracts were dried over sodium sulphate and concentrated to obtain 1.01 g of the raw product. The product was purified by chromatography on silicagel (eluent: chloroform/methanol, gradient 0-2%). 0.62 g of the title product were obtained as a creamy, crystallizing solid (yield 38%). $^1$H NMR (300 MHz, DMSO-d$_6$): δ 12.91 (s, H), 8.27 (t, J=6.8 Hz, 2H), 7.88 (d, J=8.4 Hz, 1H), 7.80-7.55 (m, 2H), 7.56-7.28 (m, 2H), 4.34 (q, J=7.1 Hz, 2H), 1.36 (t, J=7.1 Hz, 3H).

Intermediate XII-3. Ethyl 2-(1,3-thiazol-2-yl)-1H-benzimidazole-5-carboxylate

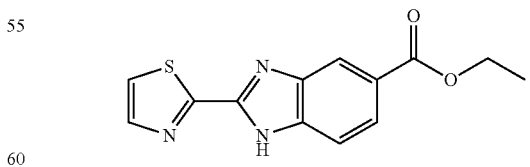

The mixture of ethyl 3,4-diaminobenzoate (2.50 g, 13.6 mmol), 2-thiazolecarboxyaldehyde (2.38 g, 20.4 mmol) and p-toluenesulphonic acid (0.517 g, 2.72 mmol) in toluene (150 mL) was heated at reflux with Dean-Stark apparatus for 3 hours. After completion of the reaction (TLC control) the whole was concentrated and chromatographed on silicagel (eluent: heptane/ethyl acetate, gradient 0-50%). 3.72 g of the solid product were obtained (yield 98%). MS-ESI: (m/z) calculated for C13H11N3O2SNa [M+Na]+: 296.05, found 296.1.

Intermediate XII-4. Ethyl 2-(1-methyl-1H-imidazol-2-yl)-1H-benzimidazole-5-carboxylate

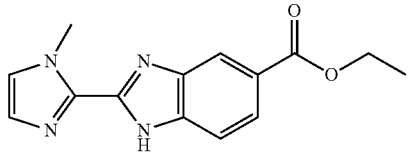 [SMILES: CCOC(=O)c1ccc2[nH]c(-c3nccn3C)nc2c1]

The mixture of ethyl 3,4-diaminobenzoate (2.0 g, 11.1 mmol) and 1-methyl-1H-imidazole-2-carboxyaldehyde (1.17 g, 10.4 mmol) in dry N,N-dimethylformamide (50 mL) was heated at 80° C. for 1 hour. Then the reaction vessel was filled with oxygen and the whole was heated under oxygen atmosphere at 120° C. for 16 hours. The mixture was concentrated, added with 100 mL of water and extracted with chloroform (4×30 mL). Extracts were dried over magnesium sulphate, filtered through celite and concentrated. The raw product was purified by chromatography on silicagel (eluent: heptane/ethyl acetate, gradient 0-90%). 1.69 g of the title product were obtained as a solid (yield 60%). MS-ESI: (m/z) calculated for $C_{14}H_{13}N_4O_2[M-H]^-$: 269.1, found 269.1.

Intermediate XII-5. Ethyl 2-benzyl-1H-benzimidazole-5-carboxylate

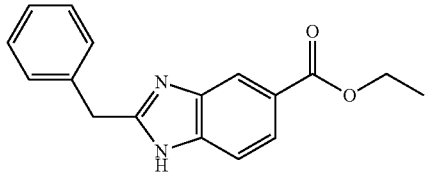 [SMILES: CCOC(=O)c1ccc2[nH]c(Cc3ccccc3)nc2c1]

The mixture of ethyl 3,4-diaminobenzoate (1.32 g, 7.34 mmol) and phenylacetic acid (1.00 g, 7.34 mmol) was put under argon and 15 mL of phosphorus oxychloride were added. The whole was heated at reflux for 3 hours. The mixture was cooled to room temperature, poured on ice and neutralized with 6M sodium hydroxide (80 mL), then brought to pH ca. 9 by 20 g of solid sodium hydrogen carbonate. 100 mL of chloroform were added and phases were separated. Aqueous phase was extracted with chloroform (2×50 mL). Combined organic phases were purified by chromatography on silicagel (eluent: chloroform/methanol, gradient 0-5%). 1.75 g of the title product were obtained as a solid (yield 85%). MS-ESI: (m/z) calculated for $C_{17}H_{15}N_2O_2[M-H]^-$: 279.1, found 279.1.

Intermediate XII-6. Ethyl 2-phenyl-3H-imidazo[4,5-c]pyridine-6-carboxylate

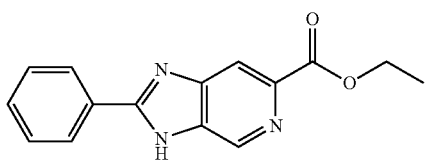 [SMILES: CCOC(=O)c1cc2nc(-c3ccccc3)[nH]c2cn1]

The compound was prepared using the method analogous as described for Intermediate XII-5. Starting from benzoic acid (0.57 g, 4.67 mmol) and ethyl 4,5-diaminopyridine-2-carboxylate (Intermediate XI-1, 0.84 g, 4.67 g) 1.15 g of the title product were obtained (yield 92%). MS-ESI: (m/z) calculated for $C_{15}H_{12}N_3O_2[M-H]^-$: 266.09, found 266.1.

Intermediates IV—Carboxylic Acids of Formula (IV)

Intermediate IV-1. 2-Phenyl-1H-benzimidazole-5-carboxylic acid

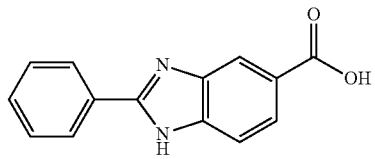 [SMILES: O=C(O)c1ccc2[nH]c(-c3ccccc3)nc2c1]

To the solution of ethyl 2-phenyl-1H-benzimidazole-5-carboxylate (Intermediate XII-1, 1.50 g, 5.63 mmol) 1.35 g of sodium hydroxide dissolved in 15 mL of water were added. The whole was heated to 60° C. for 6 hours. The reaction mixture was concentrated, cooled to 0° C. and 6M hydrochloric acid was added to obtain pH 3. Precipitated abundant white solid was filtered, washed with ethyl ether and dried under reduced pressure. 1.14 g of the title product were obtained (yield 85%). MS-ESI: (m/z) calculated for $C_{14}H_9N_2O_2[M-H]^-$: 237.2, found 237.1. The product was used for the preparation of the compounds of the invention of Examples 1 and 4.

Intermediate IV-2. 2-(2-Fluorophenyl)-1H-benzimidazole-5-carboxylic acid

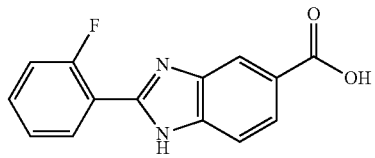 [SMILES: O=C(O)c1ccc2[nH]c(-c3ccccc3F)nc2c1]

Water (10 mL) and 0.37 g (8.72 mmol) of lithium hydroxide monohydrate were added successively to the solution of ethyl 2-(2-fluorophenyl)-1H-benzimidazole-5-carboxylate (Intermediate XII-2, 0.62 g, 2.18 mmol) in methanol (25 mL). The mixture was stirred at room temperature for 20 hours. The whole was concentrated to constant mass, solid thus obtained was dissolved in 10 mL of water and acidified with 1M hydrochloric acid to pH=6. Precipitated solid was filtered, washed successively with water and isopropanol, and dried under reduced pressure. 0.50 g of the title product were obtained (yield 91%). $^1$H NMR (300 MHz, DMSO-d$_6$): δ 12.79 (s, 1H), 8.38-8.08 (m, 2H), 7.95-7.78 (m, 1H), 7.79-7.54 (m, 2H), 7.56-7.31 (m, 2H). The product was used for the preparation of the compound of Example 2 of the invention.

Intermediate IV-50. 2-Phenyl-3H-imidazo[4,5-c]pyridine-6-carboxylic acid

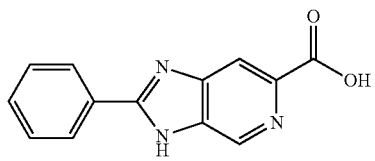 [SMILES: O=C(O)c1cc2nc(-c3ccccc3)[nH]c2cn1]

The compound was prepared analogously as Intermediate IV-1 starting from ethyl 2-phenyl-3H-imidazo[4,5-c]pyridine-6-carboxylate (Intermediate XII-6, 6.42 g, 24 mmol). 5.2 g of the title product were obtained (yield 90%). MS-ESI: (m/z) calculated for $C_{13}H_8N_3O_2[M-H]^-$: 238.06, found 238.1. The compound was used for the preparation of the compound of Example 50 of the invention.

Intermediates IV (carboxylic acids) set forth in Table 2 were obtained analogously as Intermediates IV-1 or IV-2 and used for the preparation of the corresponding compounds of the invention.

TABLE 2

| Intermediate | A | n | B-COOH | MS-ESI [M − H]⁻ |
|---|---|---|---|---|
| IV-3 | 2-pyridyl | 0 | 2-substituted benzimidazole-5-COOH | 238.1 |
| IV-4 | phenyl | 0 | 2-substituted benzimidazole-5-COOH | 237.1 |
| IV-5 | 4-pyridyl | 0 | 2-substituted benzimidazole-5-COOH | 238.1 |
| IV-6 | 3-fluorophenyl | 0 | 2-substituted benzimidazole-5-COOH | 255.1 |
| IV-7 | 4-fluorophenyl | 0 | 2-substituted benzimidazole-5-COOH | 255.1 |
| IV-8 | 2-thiazolyl | 0 | 2-substituted benzimidazole-5-COOH | 244.1 |
| IV-9 | phenyl | 1 | 2-substituted benzimidazole-5-COOH | 251.1 |
| IV-10 | phenyl | 0 | 6-fluoro-2-substituted benzimidazole-5-COOH | 255.1 |

TABLE 2-continued
| Intermediate | A | n | B-COOH | MS-ESI [M − H]⁻ |
|---|---|---|---|---|
| IV-11 | 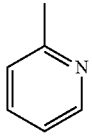 | 0 | 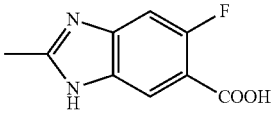 | 256.1 |
| IV-12 | 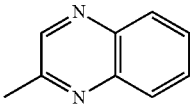 | 0 | 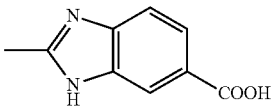 | 289.1 |
| IV-13 | 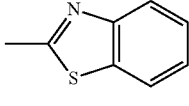 | 0 | 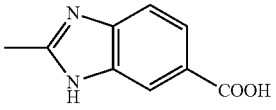 | 294.1 |
| IV-14 | 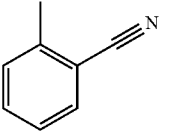 | 0 | 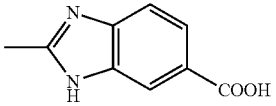 | 262.1 |
| IV-15 | 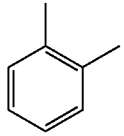 | 0 | 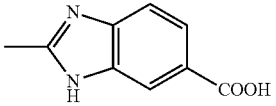 | 251.1 |
| IV-16 | 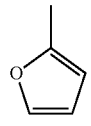 | 0 | 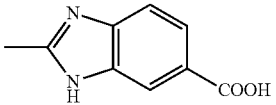 | 227.1 |
| IV-17 | 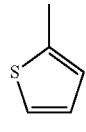 | 0 | 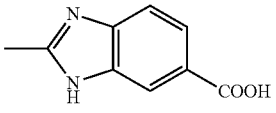 | 243.1 |
| IV-18 | 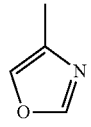 | 0 | 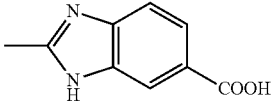 | 228.1 |
| IV-19 | 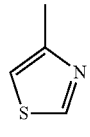 | 0 | 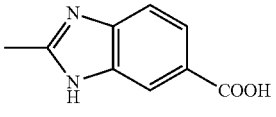 | 244.1 |
| IV-20 | 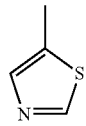 | 0 | 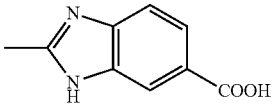 | 244.1 |
| IV-21 | 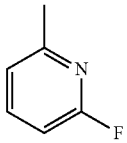 | 0 | 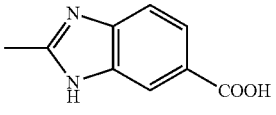 | 256.1 |

TABLE 2-continued
| Intermediate | A | n | B-COOH | MS-ESI [M − H]⁻ |
|---|---|---|---|---|
| IV-22 | 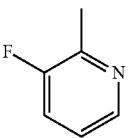 | 0 | 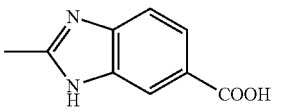 | 256.1 |
| IV-23 | 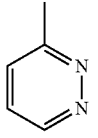 | 0 | 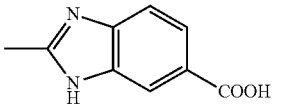 | 239.1 |
| IV-24 | 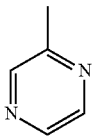 | 0 | 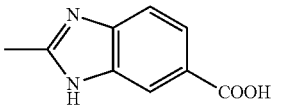 | 239.1 |
| IV-25 | 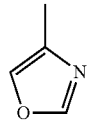 | 0 | 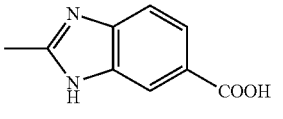 | 228.1 |
| IV-26 | 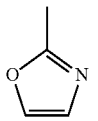 | 0 | 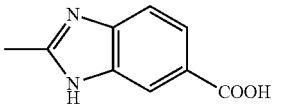 | 228.1 |
| IV-27 | 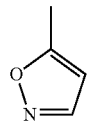 | 0 | 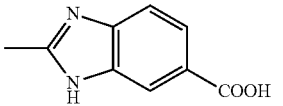 | 228.1 |
| IV-28 | 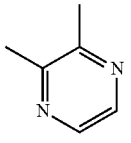 | 0 | 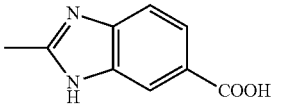 | 253.1 |
| IV-29 | 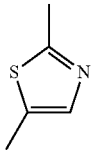 | 0 | 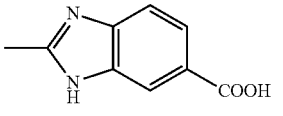 | 258.1 |
| IV-30 | 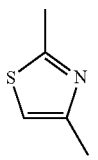 | 0 | 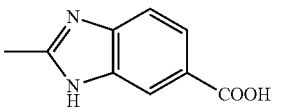 | 258.1 |
| IV-31 | 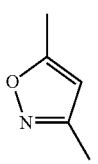 | 0 | 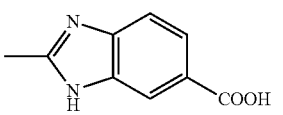 | 242.1 |

TABLE 2-continued
| Intermediate | A | n | B-COOH | MS-ESI [M − H]⁻ |
|---|---|---|---|---|
| IV-32 | 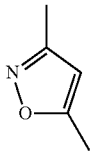 | 0 | 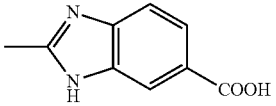 | 242.1 |
| IV-33 | 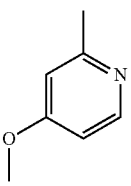 | 0 | 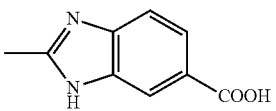 | 268.1 |
| IV-34 | 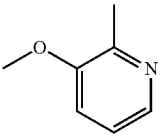 | 0 | 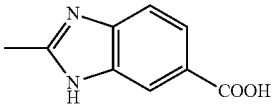 | 268.1 |
| IV-35 | 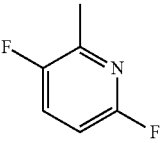 | 0 | 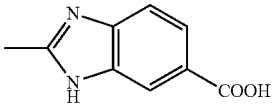 | 274.1 |
| IV-36 | 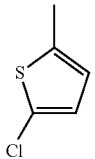 | 0 | 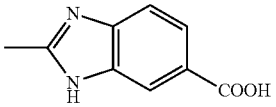 | 276.9 |
| IV-37 | 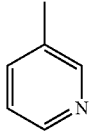 | 0 | 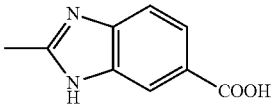 | 238.1 |
| IV-38 | 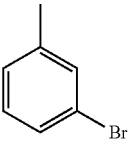 | 0 | 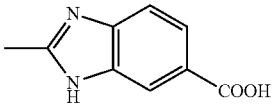 | 314.9 |
| IV-39 | 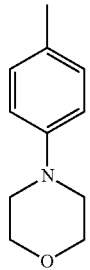 | 0 | 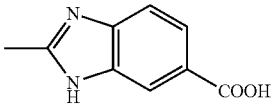 | 322.1 |
| IV-40 | 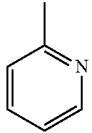 | 0 | 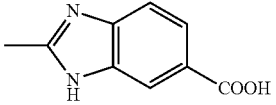 | 238.1 |

TABLE 2-continued
| Intermediate | A | n | B-COOH | MS-ESI [M − H]⁻ |
|---|---|---|---|---|
| IV-41 | 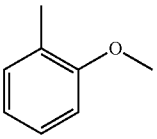 | 0 | 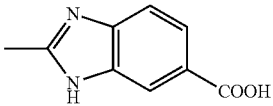 | 267.1 |
| IV-42 | 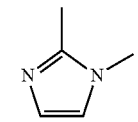 | 0 | 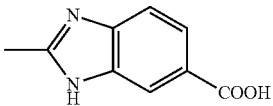 | 241.1 |
| IV-43 | 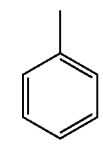 | 0 | 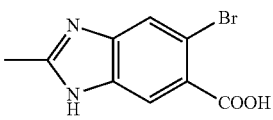 | 314.9 |
| IV-44 | 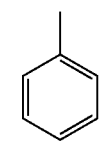 | 0 | 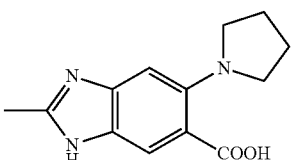 | 306.1 |
| IV-45 | 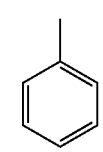 | 0 | 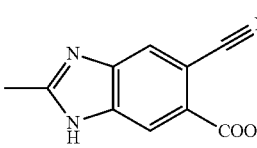 | 262.1 |
| IV-46 | 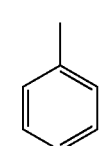 | 0 | 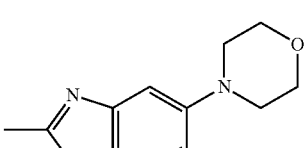 | 322.1 |
| IV-47 | 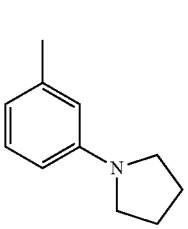 | 0 | 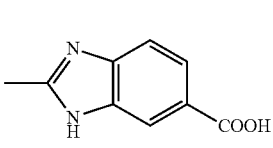 | 306.1 |
| IV-51 | 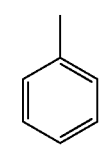 | 0 |  | 238.1 |
| IV-52 | 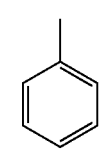 | 0 |  | 238.1 |

Intermediates XI—Diamines

Intermediate XI-1. Ethyl 4,5-diaminopyridine-2-carboxylate

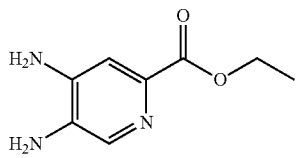

To the solution of 4-aminopicolinic acid (10.05 g, 71.3 mmol) in concentrated sulphuric acid (66 mL), potassium nitrate (7.21 g, 71.3 mmol) was added at 0° C. Orange mixture thus obtained was brought to room temperature during 30 minutes, then heated at 75° C. for further 2 hours. The mixture was cooled to 0° C. and 200 mL of absolute ethanol was slowly added dropwise. Yellow suspension thus obtained was heated at 60° C. for 12 hours. The whole was poured on ice (500 g) and neutralized with solid sodium hydroxide (49 g), then brought to pH=8 with solid sodium hydrogen carbonate. Obtained aqueous phase was extracted with chloroform (8×100 mL), combined organic extracts dried over sodium sulphate and concentrated. 10.39 g of the raw product were obtained. The product was further triturated with ethyl acetate. 8.59 g of ethyl 4-amino-5-nitropyridine-2-carboxylate as a grey solid were obtained (yield 57%). $^1$H NMR (300 MHz, DMSO-d$_6$): δ 9.03 (s, 1H), 8.27 (s, broad, 2H), 7.65 (s, 1H), 4.33 (q, J=7.1 Hz, 2H), 1.33 (t, J=7.1 Hz, 3H). MS-ESI: (m/z) calculated for $C_8H_9N_3O_4Na$ [M+Na]$^+$: 234.16, found 234.1.

To the suspension of thus obtained ethyl 4-amino-5-nitropyridine-2-carboxylate (7.59 g, 35.9 mmol) in absolute ethanol (170 mL) palladium on active carbon (0.96 g, 0.89 mmol) was added and hydrogen was introduced under normal pressure. The reaction was carried out under hydrogen atmosphere at room temperature for 18 hours. The reaction mixture was filtered through celite and washed with ethanol. After concentration 6.65 g of the solid title product were obtained (yield 100%). $^1$H NMR (300 MHz, DMSO-d$_6$): δ 7.70 (s, 1H), 7.23 (s, 1H), 5.55 (s, 2H), 5.27 (s, 2H), 4.20 (q, J=7.1 Hz, 2H), 1.37-1.19 (m, 3H). MS-ESI: (m/z) calculated for $C_8H_{11}N_3O_2Na$ [M+Na]$^+$: 204.18, found 204.1.

Intermediate XI-2. Methyl 5,6-diaminopyridine-3-carboxylate

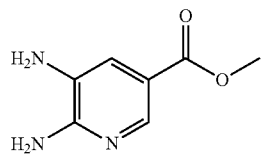

To the suspension of 5-aminonicotinic acid (10.0 g, 70.9 mmol) in concentrated sulphuric acid (25 mL) concentrated nitric acid (5.0 mL) was slowly added at 0° C. After addition of nitric acid the whole was brought to room temperature during 30 minutes, then stirred at 25° C. for 2.5 hours. Reaction mixture was poured on ice (700 g), then brought to pH=2 with 6M sodium hydroxide solution. Aqueous phase was extracted with chloroform added with 5% methanol (20×100 mL). Extracts were dried over sodium sulphate and concentrated to obtain 5.91 g of methyl 5-amino-6-nitropyridine-3-carboxylate as a solid (yield 45%). MS-ESI: (m/z) calculated for $C_6H_4N_3O_4$ [M−H]$^-$: 182.12, found 182.1.

To the suspension of thus obtained 5-amino-6-nitropyridine-3-carboxylic acid (5.91 g, 32.3 mmol) in anhydrous ethanol (120 mL) at 0° C. concentrated sulphuric acid (13.5 mL) was added and the whole was heated at 60° C. for 15 hours. The mixture was poured on ice (400 g) and neutralized with solid sodium hydroxide (20 g). The whole was concentrated and solid residue containing inorganic salts was triturated with hot methanol (200 mL). After concentration 20.1 g of methyl 5-amino-6-nitropyridine-3-carboxylate with inorganic salts were obtained. Obtained material was used in the subsequent reduction step. MS-ESI: (m/z) calculated for $C_7H_6N_3O_4$ [M−H]$^-$: 196.15, found 196.1.

To the suspension of thus obtained ethyl 5-amino-6-nitropyridine-3-carboxylate containing inorganic salts (6.36 g, 32.3 mmol) in absolute ethanol (150 mL) palladium on active carbon (0.86 g, 0.80 mmol) was added and hydrogen was introduced under normal pressure. The reaction was carried out in hydrogen atmosphere at room temperature for 48 hours. The mixture was filtered through celite and washed with ethanol. After concentration 2.70 g of the solid title product were obtained (yield 50%). MS-ESI: (m/z) calculated for $C_7H_9N_3O_2Na$ [M+Na]$^+$: 190.15, found 190.1.

Intermediate XI-3. Methyl 5,6-diaminopyridine-2-carboxylate

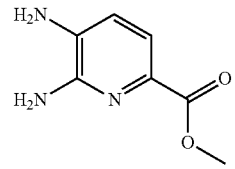

To the solution of 6-amino-5-nitro-2-picoline (12.6 g, 80.3 mmol) in dry N,N-dimethylformamide (120 mL) under argon atmosphere 25.5 g (201 mmol) of N,N-dimethylformamide (DMA) dimethyl acetal were added. The whole was heated at 110° C. for 18 hours. The mixture was concentrated to ca. ¼ of initial volume, and after addition of 60 mL of water stirred at room temperature for 16 hours. Precipitated dark-red solid was successfully washed with water and methanol and dried under reduced pressure. 6.97 g of 6-[(E)-2-(dimethylamino)-ethenyl]-3-nitropyridine-2-amine were obtained (yield 41%). MS-ESI: (m/z) calculated for $C_9H_{13}N_4O_2$ [M−H]$^-$: 209.10, found 209.1.

To thus obtained 6-[(E)-2-(dimethylamino)ethenyl]-3-nitropyridine-2-amine (5.93 g, 28.5 mmol) 105 mL of the tert-butanol/water mixture (1:1, v/v) were added. To obtained suspension solid potassium permanganate (16.1 g, 57.0 mmol) was added slowly during 10 minutes. The mixture after addition of permanganate was stirred at room temperature for 6 hours, then 60 mL of 2-propanol were added and stirring was continued overnight. 50 mL of water were then added and the whole mixture was filtered through silica gel and washed with water with the addition of sodium hydroxide to obtain pH ca. 9. The filtrate was extracted with chloroform (5×30 mL). Organic extracts were discarded, aqueous phase was acidified with 6M hydrochloric acid to pH ca. 2.5 and concentrated to constant mass. 10 mL of water were added to thus obtained solid in order to dissolve inorganic salts and obtained solid product was filtered and dried under reduced pressure. 1.43 g of methyl 6-amino-5-nitropyridine-2-carboxylate as a yellow solid were obtained (yield 27%). $^1$H NMR (300 MHz, DMSO-d$_6$): δ 8.44 (d, J=8.5 Hz, 1H), 8.05 (s, 2H), 7.25 (d, J=8.5 Hz, 1H).

To the suspension of thus obtained methyl 6-amino-5-nitropyridine-2-carboxylate (1.62 g, 8.23 mmol) in absolute ethanol (100 mL) palladium on active carbon was added (0.22 g, 0.20 mmol) and hydrogen was introduced under normal pressure. The reaction was carried out under hydrogen atmosphere at 50° C. for 12 hours. The mixture was filtered through celite and washed with ethanol. After concentration, 1.44 g of the title product as a solid were obtained (yield 100%). $^1$H NMR (300 MHz, DMSO-d$_6$): δ 7.23 (d, J=7.8 Hz, 1H), 6.68 (d, J=7.8 Hz, 1H), 5.76 (s, 2H), 5.54 (s, 2H), 3.71 (s, 3H).

Compounds of the Invention

Example 1. 5,7-Dimethyl-2-(2-phenyl-1H-benzo[d]imidazol-5-yl)-[1,2,4]triazolo-[1,5-a]pyrimidine (Method A)

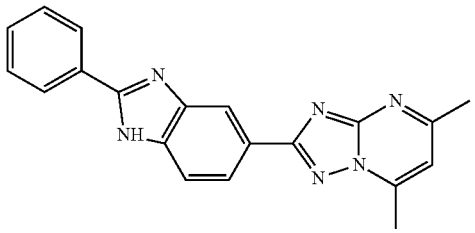 [SMILES: Cc1cc(C)n2nc(-c3ccc4[nH]c(-c5ccccc5)nc4c3)nc2n1]

To the solution of 2-phenyl-1H-benzimidazole-5-carboxylic acid (Intermediate IV-1, 0.30 g, 1.26 mmol) in dry N,N-dimethylformamide (15 mL) were added successively in a given order 1-hydroxybenzotriazole hydrate (HOBt, 0.17 g, 1.26 mmol), triethylamine (0.53 mL, 3.78 mmol), 1-amino-4,6-dimethylpyrimidin-2(1H)-iminium diphenylphosphinate (IIA, 0.45 g, 1.26 mmol) and 1-(3-dimethylaminopropyl)-3-ethylcarbodiimide hydrochloride (EDCI, 0.29 g, 1.51 mmol). The whole was put under argon and stirred at room temperature for 48 hours. The solvent (N,N-dimethylformamide) was removed under reduced pressure. To the obtained residue 15 mL of ice-cold acetic acid were added and the mixture was heated at 100° C. for 24 hours. The mixture was concentrated to about ¼ volume, then saturated aqueous hydrogen carbonate sodium solution (50 mL) and 50 mL of chloroform were added. Aqueous phase was separated and extracted with chloroform with small amount of methanol (6×40 mL). Combined organic phases were dried over sodium sulphate and concentrated. The product was purified by chromatography on silica gel (eluent: chloroform/methanol, gradient 0-10%). 0.13 g of the title product were obtained as a solid (yield 30%). $^1$H NMR (300 MHz, DMSO-d$_6$): δ 13.10 (s, 1H), 8.21 (t, J=9.9 Hz, 2H), 8.13 (d, J=8.2 Hz, 1H), 7.56 (ddd, J=15.8, 11.6, 4.2 Hz, 3H), 7.12 (d, J=0.6 Hz, 1H), 2.80 (s, 3H), 2.59 (s, 3H). MS-ESI: (m/z) calculated for C$_{20}$H$_{16}$N$_6$ [M+H]$^+$: 341.15, found 341.1.

Example 2. 2-[2-(2-Fluorophenyl)-1H-benzo[d]imidazol-5-yl]-5,8-dimethyl-[1,2,4]-triazolo[1,5-a]pyrazine (Method B)

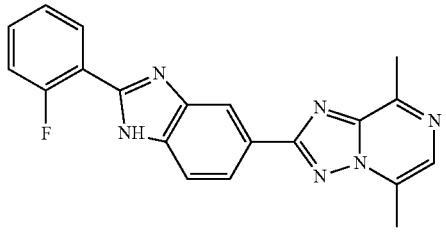 [SMILES: Cc1ncc(C)n2nc(-c3ccc4[nH]c(-c5ccccc5F)nc4c3)nc12]

To the solution of 2-(2-fluorophenyl)-1H-benzimidazole-5-carboxylic acid (Intermediate IV-2, 0.28 g, 1.09 mmol) in dry N,N-dimethylformamide (50 mL) N,N-diisopropylethylamine (0.71 g, 5.46 mmol) and HATU (0.54 g, 1.42 mmol) were added. After addition of HATU, the whole was put under argon and stirred at room temperature for 10 minutes. 1-Amino-2-imino-3,6-dimethyl-2,3-dihydro-1-pyrazinium diphenylphosphinate (IIB, 0.43 g, 1.20 mmol) was added and stirring was continued for 48 hours. The solvent was removed under reduced pressure, and the residue was chromatographed on silica gel (eluent: chloroform/ethanol, gradient 0-5%). 0.19 g of the title product were obtained as a solid (yield 50%). $^1$H NMR (300 MHz, DMSO-d$_6$): δ 12.82 (s, 1H), 8.50 (s, 1H), 8.34-8.23 (m, 1H), 8.16 (dd, J=8.4, 1.5 Hz, 1H), 7.95 (s, 1H), 7.78 (d, J=8.4 Hz, 1H), 7.67-7.54 (m, 1H), 7.46 (ddd, J=15.0, 9.4, 4.8 Hz, 2H), 2.82 (s, 3H), 2.72 (s, 3H). $^{13}$C NMR (75 MHz, DMSO-d$_6$): δ 164.11, 161.88, 158.57, 148.67, 146.93, 132.97, 132.86, 131.01, 130.8, 130.06, 125.85, 125.08, 122.33, 118.52, 118.37, 117.40, 117.11, 20.92, 14.69. MS-ESI: (m/z) calculated for C$_{20}$H$_{16}$N$_6$F [M+H]$^+$: 359.14, found 359.1.

Example 3. 5,7-Dimethyl-2-[2-(pyridin-2-yl)-1H-benzo[d]imidazol-5-yl]-[1,2,4]triazolo[1,5-a]pyrimidine (Method C)

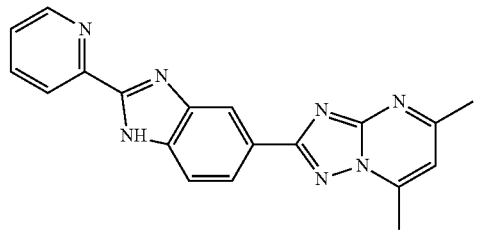 [SMILES: Cc1cc(C)n2nc(-c3ccc4[nH]c(-c5ccccn5)nc4c3)nc2n1]

The mixture of 2-(pyridin-2-yl)-1H-benzimidazole-5-carboxylic acid (Intermediate IV-40, 0.30 g, 1.25 mmol), 1-amino-4,6-dimethylpyrimidin-2(1H)-iminium diphenylphosphinate (IIA, 0.41 g, 1.14 mmol) and phosphorus oxychloride (7 mL) was heated at reflux under argon atmosphere for 3 hours. After cooling to room temperature, the mixture was poured on ice mixed with 6M sodium hydroxide (3 molar equivalents) and sodium carbonate to obtain pH=9. Aqueous phase was extracted with chloroform (5×50 mL). Extracts were dried with sodium sulphate and concentrated. The residue was chromatographed on a preparative plate (PLC Kieselgel 60 F$_{254}$, 2 mm), mobile phase: chloroform/methanol 93:7. 70 mg of the title product as two tautomeric forms were obtained (yield 18%). $^1$H NMR (300 MHz, DMSO-d$_6$): δ 13.36 (d, J=6.1 Hz, 1H), 8.78 (t, J=4.4 Hz, 1H), 8.53 (s, 1H), 8.43 (d, J=0.9 Hz, 1H), 8.38 (dd, J=7.7, 6.6 Hz, 1H), 8.18 (dd, J=8.4, 1.5 Hz, 1H), 8.13 (dd, J=8.5, 1.6 Hz, 1H), 8.04 (td, J=7.8, 1.6 Hz, 1H), 7.84 (d, J=8.5 Hz, 1H), 7.68 (d, J=8.4 Hz, 1H), 7.57 (tdd, J=7.3, 2.8, 1.7 Hz, 1H), 7.18-7.13 (m, 1H), 2.81 (s, 3H), 2.60 (s, 3H).

In Table 3 below there are presented further Examples 4 to 47 of benzimidazole compounds of the general formula (I) that were prepared analogously as in above Examples 1 to 3 starting from appropriate Intermediates IV-4 to IV-47, respectively. The compounds of Examples 4 and 5 were prepared using method A described in Example 1, compounds of Examples 6 to 39 were prepared using method B described in Example 2, and compounds of Examples 40 to 47 were prepared using method C described in Example 3.

TABLE 3

Compounds of the invention (benzimidazole derivatives)

| Ex. | Chemical name | A | n | B | R | R$^1$ | | MS-ESI [M − H]$^-$ |
|---|---|---|---|---|---|---|---|---|
| 4 | 5,8-Dimethyl-2-(2-phenyl-1H-benzimidazol-5-yl)[1,2,4]triazolo[1,5-a]pyrazine | Phenyl | 0 | B21 | H | H | C2: X$_1$ = —C(CH$_3$), X$_2$ = N | 339.1 |
| 5 | 5,7-Dimethyl-2-[3-(pyridin-4-yl)-1H-benzimidazol-5-yl][1,2,4]triazolo[1,5-a]pyrimidine | Pyridin-4-yl | 0 | B21 | H | H | C1: X$_1$ = N, X$_2$ = —C(CH$_3$) | 340.1 |
| 6 | 2-[2-(3-Fluorophenyl)-1H-benzimidazol-5-yl]-5,8-dimethyl[1,2,4]triazolo[1,5-a]pyrazine | 3-Fluorophenyl | 0 | B21 | H | H | C2: X$_1$ = —C(CH$_3$), X$_2$ = N | 357.1 |
| 7 | 2-[2-(4-FLuorophenyl)-1H-benzimidazol-5-yl]-5,8-dimethyl[1,2,4]triazolo[1,5-a]pyrazine | 4-Fluorophenyl | 0 | B21 | H | H | C2: X$_1$ = —C(CH$_3$), X$_2$ = N | 357.1 |
| 8 | 5,8-Dimethyl-2-[2-(1,3-thiazol-2-yl)-1H-benzimidazol-5-yl][1,2,4]triazolo[1,5-a]pyrazine | 1,3-Thiazol-2-yl | 0 | B21 | H | H | C2: X$_1$ = —C(CH$_3$), X$_2$ = N | 346.1 |
| 9 | 2-(2-benzyl-1H-benzimidazol-5-yl)-5,8-dimethyl[1,2,4]triazolo[1,5-a]pyrazine | Phenyl | 1 | B21 | H | H | C2: X$_1$ = —C(CH$_3$), X$_2$ = N | 353.1 |
| 10 | 2-(6-Fluoro-2-phenyl-1H-benzimidazol-5-yl)-5,8-dimethyl[1,2,4]triazolo[1,5-a]pyrazine | Phenyl | 0 | B21 | H | F | C2: X$_1$ = —C(CH$_3$), X$_2$ = N | 357.1 |
| 11 | 2-[6-Fluoro-2-(pyridin-2-yl)-1H-benzimidazol-5-yl]-5,8-dimethyl[1,2,4]triazolo[1,5-a]pyrazine | Pyridin-2-yl | 0 | B21 | H | F | C2: X$_1$ = —C(CH$_3$), X$_2$ = N | 358.1 |
| 12 | 2-[5-(5,8-Dimethyl[1,2,4]triazolo[1,5-a]pyrazin-2-yl)-1H-benzimidazol-2-yl]quinoxaline | Quinoxalin-2-yl | 0 | B21 | H | H | C2: X$_1$ = —C(CH$_3$), X$_2$ = N | 391.1 |
| 13 | 2-[2-(1,3-Benzothiazol-2-yl)-1H-benzimidazol-5-yl]-5,8-dimethyl[1,2,4]triazolo[1,5-a]pyrazine | 1,3-Benzothiazol-2-yl | 0 | B21 | H | H | C2: X$_1$ = —C(CH$_3$), X$_2$ = N | 396.1 |
| 14 | 2-[5-(5,8-Dimethyl[1,2,4]triazolo[1,5-a]pyrazin-2-yl)-1H-benzimidazol-2-yl]benzonitrile | 2-Cyanophenyl | 0 | B21 | H | H | C2: X$_1$ = —C(CH$_3$), X$_2$ = N | 364.1 |
| 15 | 5,8-Dimethyl-2-[2-(2-methylphenyl)-1H-benzimidazol-5-yl][1,2,4]triazolo[1,5-a]pyrazine | 2-Methylphenyl | 0 | B21 | H | H | C2: X$_1$ = —C(CH$_3$), X$_2$ = N | 353.1 |
| 16 | 2-[2-(Furan-2-yl)-1H-benzimidazol-5-yl]-5,8-dimethyl[1,2,4]triazolo[1,5-a]pyrazine | Furan-2-yl | 0 | B21 | H | H | C2: X$_1$ = —C(CH$_3$), X$_2$ = N | 329.1 |
| 17 | 5,8-Dimethyl-2-[2-(thiophyen-2-yl)-1H-benzimidazol-5-yl][1,2,4]triazolo[1,5-a]pyrazine | Thiophen-2-yl | 0 | B21 | H | H | C2: X$_1$ = —C(CH$_3$), X$_2$ = N | 345.1 |
| 18 | 5,8-Dimethyl-2-[2-(1,3-oxazol-4-yl)-1H-benzimidazol-5-yl][1,2,4]triazolo[1,5-a]pyrazine | 1,3-Oxazol-4-yl | 0 | B21 | H | H | C2: X$_1$ = —C(CH$_3$), X$_2$ = N | 330.1 |
| 19 | 5,8-Dimethyl-2-[2-(1,3-thiazol-4-yl)-1H-benzimidazol-5-yl][1,2,4]triazolo[1,5-a]pyrazine | 1,3-Thiazol-4-yl | 0 | B21 | H | H | C2: X$_1$ = —C(CH$_3$), X$_2$ = N | 346.1 |
| 20 | 5,8-Dimethyl-2-[2-(1,3-thiazol-5-yl)-1H-benzimidazol-5-yl][1,2,4]triazolo[1,5-a]pyrazine | 1,3-Thiazol-5-yl | 0 | B21 | H | H | C2: X$_1$ = —C(CH$_3$), X$_2$ = N | 346.1 |
| 21 | 2-[2-(6-Fluoropyridin-2-yl)-1H-benzimidazol-5-yl]-5,8-dimethyl[1,2,4]triazolo[1,5-a]pyrazine | 6-Fluoropyridin-2-yl | 0 | B21 | H | H | C2: X$_1$ = —C(CH$_3$), X$_2$ = N | 358.1 |
| 22 | 2-[2-(3-Fluoropyridin-2-yl)-1H-benzimidazol-5-yl]-5,8-dimethyl[1,2,4]triazolo[1,5-a]pyrazine | 3-Fluoropyridin-2-yl | 0 | B21 | H | H | C2: X$_1$ = —C(CH$_3$), X$_2$ = N | 358.1 |
| 23 | 5,8-Dimethyl-2-[2-(pyridin-3-yl)-1H-benzimidazol-5-yl][1,2,4]triazolo[1,5-a]pyrazine | Pyridazin-3-yl | 0 | B21 | H | H | C2: X$_1$ = —C(CH$_3$), X$_2$ = N | 341.1 |
| 24 | 5,8-Dimethyl-2-[2-(pyrazin-2-yl)-1H-benzimidazol-5-yl][1,2,4]triazolo[1,5-a]pyrazine | Pyrazin-2-yl | 0 | B21 | H | H | C2: X$_1$ = —C(CH$_3$), X$_2$ = N | 341.1 |
| 25 | 5,8-Dimethyl-2-[2-(1,3-oxazol-4-yl)-1H-benzimidazol-5-yl][1,2,4]triazolo[1,5-a]pyrazine | 1,3-Oxazol-4-yl | 0 | B21 | H | H | C2: X$_1$ = —C(CH$_3$), X$_2$ = N | 330.1 |
| 26 | 5,8-Dimethyl-2-[2-(1,3-oxazol-2-yl)-1H-benzimidazol-5-yl][1,2,4]triazolo[1,5-a]pyrazine | 1,3-Oxazol-2-yl | 0 | B21 | H | H | C2: X$_1$ = —C(CH$_3$), X$_2$ = N | 330.1 |
| 27 | 5,8-Dimethyl-2-[2-(1,2-oxazol-5-yl)-1H-benzimidazol-5-yl][1,2,4]triazolo[1,5-a]pyrazine | 1,2-Oxazol-5-yl | 0 | B21 | H | H | C2: X$_1$ = —C(CH$_3$), X$_2$ = N | 330.1 |
| 28 | 5,8-Dimethyl-2-[2-(3-methylpyrazin-2-yl)-1H-benzimidazol-5-yl][1,2,4]triazolo[1,5-a]pyrazine | 3-Methylpyrazin-2-yl | 0 | B21 | H | H | C2: X$_1$ = —C(CH$_3$), X$_2$ = N | 355.1 |
| 29 | 5,8-Dimethyl-2-[2-(5-methyl-1,3-thiazol-2-yl)-1H-benzimidazol-5-yl][1,2,4]triazolo[1,5-a]pyrazine | 5-Methyl-1,3-thiazol-2-yl | 0 | B21 | H | H | C2: X$_1$ = —C(CH$_3$), X$_2$ = N | 360.1 |
| 30 | 5,8-Dimethyl-2-[2-(4-methyl-1,3-thiazol-2-yl)-1H-benzimidazol-5-yl][1,2,4]triazolo[1,5-a]pyrazine | 4-Methyl-1,2-thiazol-2-yl | 0 | B21 | H | H | C2: X$_1$ = —C(CH$_3$), X$_2$ = N | 360.1 |
| 31 | 5,8-Dimethyl-2-[2-(3-methyl-1,2-oxazol-5-yl)-1H-benzimidazol-5-yl][1,2,4]triazolo[1,5-a]pyrazine | 3-Methyl-1,2-oxazol-5-yl | 0 | B21 | H | H | C2: X$_1$ = —C(CH$_3$), X$_2$ = N | 344.1 |
| 32 | 5,8-Dimethyl-2-[2-(5-methyl-1,2-oxazol-3-yl)-1H-benzimidazol-5-yl][1,2,4]triazolo[1,5-a]pyrazine | 5-Methyl-1,2-oxazol-3-yl | 0 | B21 | H | H | C2: X$_1$ = —C(CH$_3$), X$_2$ = N | 344.1 |

TABLE 3-continued

Compounds of the invention (benzimidazole derivatives)

| Ex. | Chemical name | A | n | B | R | R¹ | | MS-ESI [M − H]⁻ |
|---|---|---|---|---|---|---|---|---|
| 33 | 2-[2-(4-Methoxypyridin-2-yl)-1H-benzimidazol-5-yl]-5,8-dimethyl[1,2,4]triazolo[1,5-a]pyrazine | 4-Methoxy-pyridin-2-yl | 0 | B21 | H | H | C2: $X_1 = -C(CH_3)$, $X_2 = N$ | 370.1 |
| 34 | 2-[2-(3-Methoxypyridin-2-yl)-1H-benzimidazol-5-yl]-5,8-dimethyl[1,2,4]triazolo[1,5-a]pyrazine | 3-Methoxy-pyridin-2-yl | 0 | B21 | H | H | C2: $X_1 = -C(CH_3)$, $X_2 = N$ | 370.1 |
| 35 | 2-[2-(3,6-Difluoropyridin-2-yl)-1H-benzimidazol-5-yl]-5,8-dimethyl[1,2,4]triazolo[1,5-a]pyrazine | 3,6-Difluoro-pyridin-2-yl | 0 | B21 | H | H | C2: $X_1 = -C(CH_3)$, $X_2 = N$ | 376.1 |
| 36 | 2-[2-(5-Chlorothiophen-2-yl)-1H-benzimidazol-5-yl]-5,8-dimethyl[1,2,4]triazolo[1,5-a]pyrazine | 5-Chloro-thiophen-2-yl | 0 | B21 | H | H | C2: $X_1 = -C(CH_3)$, $X_2 = N$ | 379.1 |
| 37 | 5,8-Dimethyl-2-[2-(pyridin-3-yl)-1H-benzimidazol-5-yl][1,2,4]triazolo[1,5-a]pyrazine | Pyridin-3-yl | 0 | B21 | H | H | C2: $X_1 = -C(CH_3)$, $X_2 = N$ | 340.1 |
| 38 | 2-[2-(3-Bromophenyl)-1H-benzimidazol-5-yl]-5,8-dimethyl[1,2,4]triazolo[1,5-a]pyrazine | 3-Bromophenyl | 0 | B21 | H | H | C2: $X_1 = -C(CH_3)$, $X_2 = N$ | 417.1 |
| 39 | 4-(4-(5-(5,8-Dimethyl[1,2,4]triazolo[1,5-a]pyrazin-2-yl)-1H-benzimidazol-2-yl)phenyl)morpholine | 4-Phenyl-morpholinyl | 0 | B21 | H | H | C2: $X_1 = -C(CH_3)$, $X_2 = N$ | 424.2 |
| 40 | 5,8-Dimethyl-2-[2-(pyridin-2-yl)-1H-benzimidazol-5-yl][1,2,4]triazolo[1,5-a]pyrazine | Pyridin-2-yl | 0 | B21 | H | H | C2: $X_1 = -C(CH_3)$, $X_2 = N$ | 340.1 |
| 41 | 2-[2-(2-Methoxyphenyl)-1H-benzimidazol-5-yl]-5,8-dimethyl[1,2,4]triazolo[1,5-a]pyrazine | 2-Methoxy-phenyl | 0 | B21 | H | H | C2: $X_1 = -C(CH_3)$, $X_2 = N$ | 369.1 |
| 42 | 5,8-Dimethyl-2-[2-(1-methyl-1H-imidazol-2-yl)-1H-benzimidazol-5-yl][1,2,4]triazolo[1,5-a]pyrazine | 1-Methyl-1H-imidazol-2-yl | 0 | B21 | H | H | C2: $X_1 = -C(CH_3)$, $X_2 = N$ | 343.1 |
| 43 | 2-(6-Bromo-2-phenyl-1H-benzimidazol-5-yl)-5,8-dimethyl[1,2,4]triazolo[1,5-a]pyrazine | 6-Bromophenyl | 0 | B21 | H | Br | C2: $X_1 = -C(CH_3)$, $X_2 = N$ | 417.1 |
| 44 | 5,8-Dimethyl-2-(2-phenyl-6-(pyrrolidin-1-yl)-1H-benzimidazol-5-yl)-[1,2,4]triazolo[1,5-a]pyrazine | Phenyl | 0 | B21 | H | Pyrrolidin-1-yl | C2: $X_1 = -C(CH_3)$, $X_2 = N$ | 408.1 |
| 45 | 5-(5,8-Dimethyl[1,2,4]triazolo[1,5-a]pyrazin-2-yl)-2-phenyl-1H-benzimidazolo-6-carbonitrile | Phenyl | 0 | B21 | H | CN | C2: $X_1 = -C(CH_3)$, $X_2 = N$ | 364.1 |
| 46 | 4-(5-(5,8-Dimethyl[1,2,4]triazolo[1,5-a]pyrazin-2-yl)-2-phenyl-1H-benzimidazol-6-yl)morpholine | Phenyl | 0 | B21 | H | Morpholin-4-yl | C2: $X_1 = -C(CH_3)$, $X_2 = N$ | 424.1 |
| 47 | 5,8-Dimethyl-2-(2-(3-(pyrrolidin-1-yl)phenyl)-1H-benzimidazol-[1,2,4]triazolo[1,5-a]pyrazine | 3-(Pyrrolidin-1-yl)phenyl | 0 | B21 | H | H | C2: $X_1 = -C(CH_3)$, $X_2 = N$ | 408.1 |

Example 48A. 5,7-Dimethyl-2-(1-methyl-2-phenyl-1H-benzo[d]imidazol-5-yl)-[1,2,4]-triazolo[1,5-a]pyrimidine

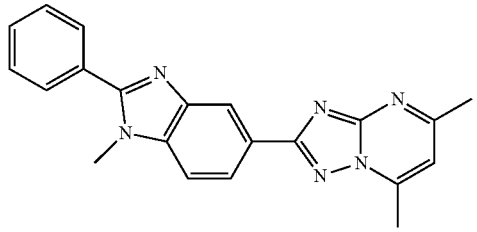 [SMILES: Cc1cc(C)n2nc(-c3ccc4c(c3)nc(-c3ccccc3)n4C)nc2n1]

and

Example 48B. 5,7-Dimethyl-2-(1-methyl-2-phenyl-1H-benzo[d]imidazol-6-yl)-[1,2,4]-triazolo[1,5-a]pyrimidine

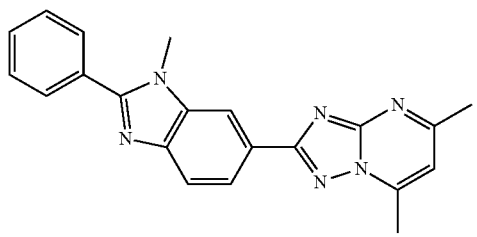 [SMILES: Cc1cc(C)n2nc(-c3ccc4nc(-c5ccccc5)n(C)c4c3)nc2n1]

To the solution of 5,7-dimethyl-2-(2-phenyl-1H-benzo[d]imidazol-5-yl)-[1,2,4]triazolo-[1,5-a]pyrimidine (Example 1, 80 mg, 0.23 mmol) in dry N,N-dimethylformamide (3.5 mL) potassium carbonate (65 mg, 0.47 mmol) was added. The whole was put under argon and after 10 minutes methyl iodide (0.03 mL, 0.47 mmol) was added. The reaction was carried out for 24 hours at room temperature. To the mixture water (10 mL) and ethyl acetate (20 mL) were added. Aqueous phase was separated and extracted with ethyl acetate (4×20 mL). Combined extracts were dried with sodium sulphate and concentrated. The residue was chromatographed on a preparative plate (PLC Kieselgel 60 F$_{254}$, 2 mm), mobile phase: chloroform/methanol 95:5. 47 mg of the compound 48A and 40 mg of the compound 48B were obtained as solids (yields 48 and 56%, respectively).

Compound 48A, ¹H NMR (300 MHz, DMSO-d$_6$): δ 8.51 (d, J=1.0 Hz, 1H), 8.22 (dd, J=8.4, 1.5 Hz, 1H), 7.90 (dd, J=7.7, 1.8 Hz, 2H), 7.79 (d, J=8.4 Hz, 1H), 7.64-7.57 (m, 3H), 7.17 (s, 1H), 3.94 (s, 3H), 2.82 (s, 3H), 2.61 (d, J=6.8 Hz, 3H).

Compound 48B, ¹H NMR (300 MHz, DMSO-d$_6$): δ 8.42 (d, J=1.0 Hz, 1H), 8.18 (dd, J=8.4, 1.5 Hz, 1H), 7.89 (dt, J=4.3, 2.3 Hz, 2H), 7.82 (d, J=8.4 Hz, 1H), 7.65-7.57 (m, 3H), 738 (d, J=0.8 Hz, 1H), 3.99 (s, 3H), 2.82 (s, 3H), 2.61 (s, 3H).

Example 49A. 5,7-Dimethyl-2-[1-methyl-2-(pyridin-2-yl)-1H-benzo[d]imidazol-5-yl]-[1,2,4]triazolo[1,5-a]pyrimidine

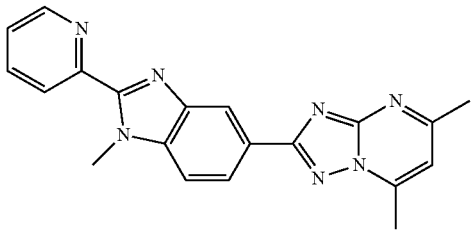 [SMILES: Cc1cc(C)n2nc(-c3ccc4c(c3)nc(-c3ccccn3)n4C)nc2n1]

and

Example 49B. 5,7-Dimethyl-2-[1-methyl-2-(pyridin-2-yl)-1H-benzo[d]imidazol-6-yl]-[1,2,4]triazolo[1,5-a]pyrimidine

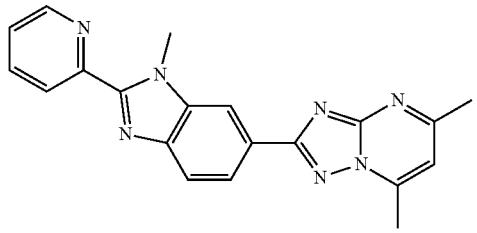 [SMILES: Cc1cc(C)n2nc(-c3ccc4nc(-c5ccccn5)n(C)c4c3)nc2n1]

Using the method analogous to that described in Example 48A/B and starting from 5,7-dimethyl-2-[2-(pyridin-2-yl)-1H-benzo[d]imidazol-5-yl]-[1,2,4]triazolo[1,5-a]pyrimidine (Example 3, 49 mg, 0.14 mmol), potassium carbonate (40 mg, 0.29 mmol) and methyl iodide (41 mg, 0.29 mmol), 16 mg of the compound 49A and 12 mg of the compound 49B were obtained as solids (yields 63 and 47%, respectively).

Compound 49A, $^1$H NMR (300 MHz, CDCl$_3$): δ 8.83-8.69 (m, 1H), 8.44-8.26 (m, 2H), 7.93 (td, J=7.8, 1.8 Hz, 1H), 7.58 (d, J=8.1 Hz, 1H), 7.42 (ddd, J=7.6, 4.8, 1.1 Hz, 1H), 7.32 (s, 1H), 6.82 (d, J=0.8 Hz, 1H), 4.33 (d, J=20.0 Hz, 3H), 2.87 (s, 3H), 2.67 (s, 3H).

Compound 49B, $^1$H NMR (300 MHz, CDCl$_3$): δ 8.75 (ddd, J=4.8, 1.7, 0.9 Hz, 1H), 8.54-8.46 (m, 1H), 8.41-8.27 (m, 2H), 7.91 (tt, J=5.1, 3.2 Hz, 2H), 7.51-7.38 (m, 1H), 6.84 (d, J=0.8 Hz, 1H), 4.35 (d, J=5.6 Hz, 3H), 2.88 (s, 3H), 2.68 (s, 3H).

Example 50. 5,8-Dimethyl-2-(2-phenyl-3H-imidazo[4,5-c]pyridin-6-yl)[1,2,4]triazolo-[1,5-a]pyrazine

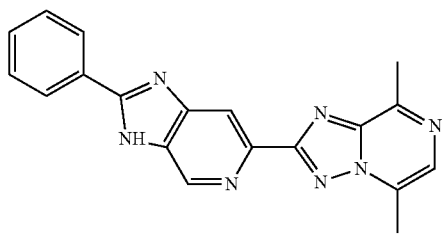 [SMILES: Cc1ncc(C)n2nc(-c3cc4nc(-c5ccccc5)[nH]c4cn3)nc12]

Using the method analogous to that described in Example 2 and starting from 2-phenyl-3H-imidazo[4,5-c]pyridin-6-carboxylic acid (Intermediate IV-50, 0.60 g, 2.52 mmol) and 1-amino-2-imino-3,6-dimethyl-2,3-dihydro-1-pyrazinium diphenylphosphinate (IIB) (0.93 g, 2.64 mmol), 0.27 g of the title product were obtained (yield 31%). $^1$H NMR (300 MHz, DMSO-d$_6$): δ 9.06 (s, 1H), 8.43 (s, 1H), 8.24 (d, J=6.5 Hz, 2H), 8.00 (s, 1H), 7.60 (d, J=7.1 Hz, 3H), 2.84 (s, 3H), 2.75 (s, 3H). $^{13}$C NMR (75 MHz, DMSO-d$_6$): δ 164.04, 155.69, 149.18, 146.82, 141.92, 139.95, 131.50, 131.06, 130.23, 130.14, 129.79, 127.79, 109.03, 20.95, 14.74. MS-ESI: (m/z) calculated for C$_{19}$H$_{14}$N$_7$ [M-H]$^-$: 340.38, found 340.1.

Example 51. 5,8-Dimethyl-2-(2-phenyl-3H-imidazo[4,5-b]pyridin-6-yl)-[1,2,4]triazolo-[1,5-a]pyrazine

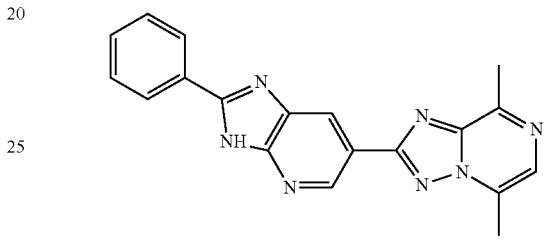

Using the method analogous to that described in Example 2 and starting from 2-phenyl-1H-imidazo[4,5-b]pyridin-6-carboxylic acid (Intermediate IV-51, 0.70 g, 2.91 mmol) and 1-amino-2-imino-3,6-dimethyl-2,3-dihydro-1-pyrazinium diphenylphosphinate (IIB, 0.73 g, 3.05 mmol), 0.21 g of the title product were obtained (yield 19%). MS-ESI: (m/z) calculated for C$_{19}$H$_{14}$N$_7$ [M-H]$^-$ 340.38, found 340.1.

Example 52. 5,8-Dimethyl-2-(2-phenyl-1H-imidazo[4,5-b]pyridin-5-yl)[1,2,4]triazolo-[1,5-a]pyrazine

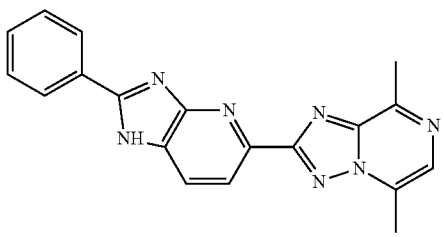 [SMILES: Cc1ncc(C)n2nc(-c3ccc4[nH]c(-c5ccccc5)nc4n3)nc12]

Using the method analogous to that described in Example 2, and starting from 2-phenyl-3H-imidazo[4,5-b]pyridin-5-carboxylic acid (Intermediate IV-52, 0.76 g, 3.16 mmol) and 1-amino-2-imino-3,6-dimethyl-2,3-dihydro-1-pyrazinium diphenylphosphinate (IIB, 1.18 g, 3.32 mmol), 0.29 g of the title product were obtained (yield 27%). $^1$H NMR (300 MHz, DMSO-d$_6$): δ 13.97 (s, 1H), 8.19 (dd, J=14.8, 8.4 Hz, 2H), 7.97 (s, 1H), 7.57 (m, 5H), 2.80 (s, 3H), 2.72 (s, 3H). MS-ESI: (m/z) calculated for C$_{19}$H$_{14}$N$_7$ [M-H]$^-$: 340.38, found 340.1.

Following the procedure of in Example 51 and using suitable Intermediates, compounds of the invention presented in Table 4 below were prepared.

TABLE 4

Compounds of the invention (azabenzimidazole derivatives)

| Ex. | Chemical name | A | n | B | R | R¹ | | MS-ESI [M − H]⁻ |
|---|---|---|---|---|---|---|---|---|
| 53 | 6,8-Dimethyl-2-(2-phenyl-1H-imidazo[4,5-c]pyridin-6-yl)[1,2,4]triazolo[1,5-a]pyrazine | phenyl | 0 | B23 | H | H | C1: $X_1$ = N, $X_2$ = —C(CH₃) | 340.1 |
| 54 | 6,8-Dimethyl-2-(2-phenyl-1H-imidazo[4,5-b]pyridin-6-yl)[1,2,4]triazolo[1,5-a]pyrazine | phenyl | 0 | B22 | H | H | C1: $X_1$ = N, $X_2$ = —C(CH₃) | 340.1 |
| 55 | 6,8-Dimethyl-2-(2-phenyl-3H-imidazo[4,5-b]pyridin-5-yl)[1,2,4]triazolo[1,5-a]pyrazine | phenyl | 0 | B24 | H | H | C1: $X_1$ = N, $X_2$ = —C(CH₃) | 340.1 |

Example 56. 5,7-Dimethyl-2-(2-phenylimidazo[1,2-a]pyrimidin-7-yl)[1,2,4]triazolo-[1,5-a]pyrimidine

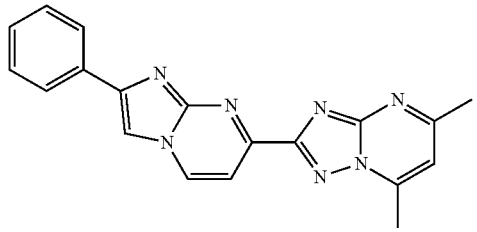 [SMILES: Cc1cc(C)n2nc(-c3ccn4cc(-c5ccccc5)nc4n3)nc2n1]

To the solution of 2-phenylimidazo[1,2-a]pyrimidino-7-carboxyaldehyde (Intermediate III-1, 0.18 g, 0.78 mmol) in dry N,N-dimethylformamide (10 mL) 1-amino-4,6-dimethylpyrimidine-2(1H)-iminium diphenylphosphinate ((IIA), 0.34 g, 0.96 mmol) was added under argon atmosphere. After heating the whole at 80° C. for 3 hours, the reaction was continued at 50° C. for 48 hours, with vigorous stirring and in the air atmosphere. The mixture was added with toluene (5 mL) and concentrated to about ¼ volume under reduced pressure. Residue thus obtained was filtered through celite and chromatographed on silica gel (eluent: chloroform/methanol 95:5). 57 mg of the title product as a solid were obtained (yield 21%). ¹H NMR (300 MHz, DMSO-$d_6$): δ 9.12 (d, J=7.0 Hz, 1H), 8.53 (s, 1H), 8.07 (d, J=7.5 Hz, 2H), 7.88 (d, J=6.9 Hz, 1H), 7.52 (t, J=7.6 Hz, 2H), 7.41 (t, J=6.9 Hz, 1H), 7.25 (s, 1H), 2.81 (d, J=16.8 Hz, 3H), 2.64 (s, 3H).

Further Examples 57 to 63 of imidazopyrimidine compounds of the general formula (I), prepared analogously as in Example 56 using suitable Intermediates, are presented in Table 5 below.

TABLE 5

The compounds of the invention (imidazopyrimidine derivatives)

| Ex. | Chemical name | A | n | B | | MS-ESI [M + Na]⁺ |
|---|---|---|---|---|---|---|
| 57 | 5,8-Dimethyl-2-(2-phenylimidazo[1,2-a]pyrimidin-7-yl)[1,2,4]triazolo[1,5-a]pyrazine | Phenyl | 0 | B1 | C2: $X_1$ = —C(CH₃), $X_2$ = N | 364.3 |
| 58 | 5,7-Dimethyl-2-[2-(pyridin-2-yl)imidazo1,2-a]pyrimidin-7-yl][1,2,4]triazolo[1,5-a]pyrazine | Pyridin-2-yl | 0 | B1 | C1: $X_1$ = N, $X_2$ = —C(CH₃) | 365.3 |
| 59 | 5,7-Dimethyl-2-[2-(1,3-thiazol-2-yl)imidazo[1,2-a]pyrimidin-7-yl][1,2,4]triazolo[1,5-a]pyrazine | 1,3-Thiazol-2-yl | 0 | B1 | C1: $X_1$ = N, $X_2$ = —C(CH₃) | 371.3 |
| 60 | 2-[2-(2-Methoxyphenyl)imidazo[1,2-a]pyrimidin-7-yl]-5,8-dimethyl[1,2,4]triazolo[1,5-a]pyrazine | 2-Methoxyphenyl | 0 | B1 | C2: $X_1$ = —C(CH₃), $X_2$ = N | 394.3 |
| 61 | 5,8-Dimethyl-2-[2-(1,3-thiazol-2-yl)imidazo[1,2-a]-pyrimidin-7-yl][1,2,4]triazolo[1,5-a]pyrazine | 1,3-Thiazol-2-yl | 0 | B1 | C2: $X_1$ = —C(CH₃), $X_2$ = N | 371.3 |
| 62 | 5,8-Dimethyl-2-[2-(pyridin-2-yl)imidazo[1,2-a]pyrimidin-7-yl][1,2,4]triazolo[1,5-a]pyrazine | Pyridin-2-yl | 0 | B1 | C2: $X_1$ = —C(CH₃), $X_2$ = N | 365.3 |
| 63 | 2-[2-(5-Chlorothiophen-2-yl)imidazo[1,2-a]pyrimidin-7-yl]-5,8-dimethyl[1,2,4]triazolo[1,5-a]pyrazine | 5-Chlorothiophen-2-yl | 0 | B1 | C2: $X_1$ = —C(CH₃), $X_2$ = N | 404.8 |
| 64 | 5,8-Dimethyl-2-[2-(thiophen-2-yl)imidazo[1,2-a]-pyrimidin-7-yl][1,2,4]triazolo[1,5-a]pyrazine | Thiophen-2-yl | 0 | B1 | C2: $X1$ = —C(CH₃), $X2$ = N | 370.1 |
| 65 | 2-[2-(5-Chlorothiophen-2-yl)imidazo[1,2-a]pyrimidin-7-yl]-5,8-dimethyl[1,2,4]triazolo[1,5-a]pyrazine | 5-Chlorothiophen-2-yl | 0 | B1 | C2: $X1$ = —C(CH₃), $X2$ = N | 404.8 |
| 66 | 2-[2-(3-Bromophenyl)imidazo[1,2-a]pyrimidin-7-yl]-5,8-dimethyl[1,2,4]triazolo[1,5-a]pyrazine | 3-Bromophenyl | 0 | B1 | C2: $X1$ = —C(CH₃), $X2$ = N | 443.1 |
| 67 | 5,8-Dimethyl-2-[2-(3-(pyrrolidin-1-yl)phenyl)imidazo[1,2-a]pyrimidin-7-yl][1,2,4]triazolo[1,5-a]pyrazine | 3-(pyrrolidin-1-yl)phenyl | 0 | B1 | C2: $X1$ = —C(CH₃), $X2$ = N | 433.1 |
| 68 | 2-(6-Bromo-2-phenylimidazo[1,2-a]pyrimidin-7-yl)-5,8-dimethyl[1,2,4]triazolo[1,5-a]pyrazine | Phenyl | 0 | B1 | C2: $X1$ = —C(CH₃), $X2$ = N | 443.1 |
| 69 | 5,8-Dimethyl-2-[2-phenyl-6-(pyrrolidin-1-yl)imidazo[1,2-a]pyrimidin-7-yl][1,2,4]triazolo[1,5-a]pyrazine | Phenyl | 0 | B1 | C2: $X1$ = —C(CH₃), $X2$ = N | 433.1 |

TABLE 5-continued

The compounds of the invention (imidazopyrimidine derivatives)

$$\text{[structure: methyl-triazolo fused bicyclic with } X_1, X_2 \text{ substituents]}$$

| Ex. | Chemical name | A | n | B | MS-ESI [M + Na]+ |
|-----|---------------|---|---|---|------------------|
| 70 | 4-[7-(5,8-Dimethyl-[1,2,4]triazolo[1,5-a]pyrazin-2-yl)-2-phenylimidazo[1,2-a]pyrimidin-6-yl]morpholine | Phenyl | 0 | B1 C2: X1 = —C(CH$_3$), X2 = N | 449.1 |
| 71 | 5,8-Dimethyl-2-[6-(4-methylpiperazin-1-yl)-2-phenyl-imidazo[1,2-a]pyrimidin-7-yl][1,2,4]triazolo[1,5-a]pyrazine | Phenyl | 0 | B1 C2: X1 = —C(CH$_3$), X2 = N | 462.1 |
| 72 | 7-(5,8-Dimethyl[1,2,4]triazolo[1,5-a]pyrazin-2-yl)-2-phenylimidazo[1,2-a]pyrimidino-6-carbonitrile | Phenyl | 0 | B1 C2: X1 = —C(CH$_3$), X2 = N | 389.1 |

Biological Examples

The activity of the compounds of the invention was tested using the following biological methods.

1. Assay of Phosphodiesterase 10 Inhibition In Vitro

Recombinant human phosphodiesterase 10A (PDE10A) purified to homogeneity from Sf9 cells overexpressing PDE10A gene (GenBank/EMBL accession number: NM_001130690) was used for inhibition tests.

Inhibitory activity of the compounds towards PDE10A was tested using PDE-Glo (Promega Corporation, Madison, USA) luminescent method on 96-well plates. Test was performed for 8 concentrations of the compounds. Test compounds were dissolved in 100% DMSO and resulted solutions were diluted 5× in concentrated PDE-Glo Reaction Buffer. Eight concentrations of each tested compound were obtained by subsequent dilution. 5 μl of obtained solutions were added into the wells of 96-well plate. Next, 7.5 μl of a solution containing PDE9A enzyme diluted in 1× concentrated PDE-Glo Reaction Buffer were added into the well to obtain the final amount of 2-10 ng (depending on the activity of the enzyme batch used in the study). In order to facilitate interaction between compounds and the enzyme, plates were incubated for 1 minute at room temperature and then 9 minutes at 4° C. Reaction was initiated by addition of 12.5 μl of 2 μM cAMP solution into the well and subsequently plate was incubated at 30° C.

After 40 minutes reaction was stopped by addition of 12.5 μl of PDE-Glo Termination Buffer with high concentration of a known PDE10 inhibitor. Plate content was stirred with orbital shaker at 500 RPMs for 10 minutes and then in the next step 12.5 μl of freshly prepared PDE-Glo Detection Solution were added into the well.

Plate was incubated for 20 minutes at room temperature before 50 μl of Kinase Glo reagent (Promega Corporation, Madison, USA) was applied into the wells and incubation at room temperature was continued for the next 10 minutes. After incubation, luminescence intensity in wells was measured with the Victor Light (Perkin Elmer Inc.) luminometer.

Percent of PDE10A inhibition by tested compounds was determined based on luminescence intensity measurements in wells containing test compounds and in control wells. Results were then fitted using a four-parameter logistic fit in GraphPad Prism 5.03 software (GraphPad Software Inc.). Negative control wells contained all above mentioned reagents except test compounds and positive control wells contained all above mentioned reagents except test compounds and the PDE10A enzyme. Each chemical compound was assayed in at least two independent runs (2×96-well plate in duplicate) with at least 3 wells of each of the controls.

The results obtained in the test show that the compounds of the invention inhibit PDE10A at IC$_{50}$ lower than 800 nM. Averaged IC$_{50}$ values for representative compounds of the invention are presented below in Table 6.

TABLE 6

| Example | hPDE10A1 IC$_{50}$ (nM) |
|---------|------------------------|
| 1 | 47 |
| 2 | 37 |
| 3 | 279 |
| 4 | 27 |
| 5 | 953 |
| 6 | 172 |
| 7 | 54 |
| 8 | 84 |
| 40 | 63 |
| 41 | 19.5 |
| 48A | 794 |
| 48B | 413 |
| 56 | 96 |
| 57 | 35.7 |

2. Assessment of Phosphorylation of Ser845 Residue on Striatal AMPA Receptor GluR1 Subunit in Rats.

The level of phosphorylation of GluR1 subunit of AMPA receptor on Ser845 (S845) in rat striatum was determined to assess the effect of compounds of the invention on the biochemical processes in striatum. Phosphorylation of GluR1 on Ser845 residue is catalysed by protein kinase A (PKA) and protein kinase G (PKG) in response to elevated level of cAMP and cGMP, respectively, in cytosol. Said phosphorylation of GluR1 subunit triggers translocation of AMPA receptors to cell membrane and increase probability of its opening, thus strengthening glutamatergic signaling and influencing the synaptic plasticity.

The compounds of the invention were administered p.o. to male Wistar rats (250-300 g) in a dose of 10 mg/kg body weight. The animals were sacrificed under Isoflurane anesthesia 30 minutes after administration. Stratia were dissected from collected brain tissues and immediately homogenized in RIPA lysis buffer (Sigma-Aldrich) containing phosphatase inhibitors (PhosSTOP, Roche) and protease inhibitors (Halt Protease Inhibitor Single-Use Coctail, Thermo Scientific). Homogenates were centrifuged and supernatants were used for immunobloting analysis to assess the phosphorylation level of GluR1 subunit on Ser845 residue. β-Tubulin was used as a loading control.

Oral administration of the compounds of the invention resulted in 3-10 times increase of phosphorylation on the Ser845 residue of GluR1 subunit in rat striatum compared to animals that received only vehicle. Results obtained in this experiment for exemplary compounds of the invention are presented in FIG. 1.

3. Metabolic Stability

To preliminary assess metabolic stability in liver, comparative metabolic stability assay was performed for a group of representative, structurally diversified compounds of the invention and structurally close the most active example compound from WO2013003298.

Tested compounds were incubated in triplicates with rat liver microsomal fraction at 37° C. in the presence of metabolic phase I cofactors (NADP, G6P, G6P dehydrogenase, $MgCl_2$) necessary for metabolic transformations. Concentration of a non-metabolized tested compound in the reaction mixture was measured using LC/MS method at 4 time points: after 0, 20, 40 and 60 min of incubation. The AUC of compounds at those time points were compared with AUC at point 0 to obtain % loss of parental compound. The obtained data were used for calculation of internal clearance (Cl(int)) and half-life (T½). The metabolic activity of microsomes was assessed by measuring the stability of two standards with low and high metabolic stability, propranolol and donepezil, respectively. The results (T½ and Cl(int)) for the selected compounds of the invention are shown in the Table 7 below.

Values of both internal clearance and half-life of presented compounds show that compounds of the invention have almost twice higher metabolic stability comparing to the Example No. 1 from WO2013003298.

4. Test of Phencyclidine Induced Hyperlocomotion (PCP) in Rats

Test of PCP-induced hyperlocomotion was performed on the male Sprague-Dawley rats (Charles River, Germany) weighing ~250 g at the arrival. The animals were housed in the standard laboratory cages, under standard colony A/C controlled conditions: room temperature 21±2° C., humidity (40-50%), 12 hours light/dark cycle (lights on: 06:00) with ad libitum access to food and water. Rats were allowed to acclimatize for at least 7 days before the start of the experimental procedure. During that week animals were handled for at least 3 times.

1 hour before the start of the experiment, the rats were transferred to the experimental room for acclimation. Tested compounds were administered p.o. in the volume of 1 mL/kg 30 minutes before placing the animals individually into the auto-tracks for 60 minutes of spontaneous locomotor activity measurement. Thereafter, the rats were injected s.c. with PCP at a dose of 5 mg/kg and then the PCP-induced locomotor activities were measured for the following 150 minutes.

Spontaneous and PCP-induced locomotor activity were measured automatically in Opto-Varimex-4 Auto-Tracks (Columbus Instruments, Ohio, USA) located in sound-attenuated and ventilated boxes.

TABLE 7

| Compound | Structure | $T_{1/2}$ min | Cl(int) ul/min/mg |
|---|---|---|---|
| Ex. 4 | 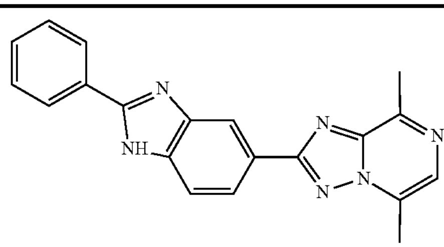 | 62.78 | 36.79 |
| Ex. 57 | 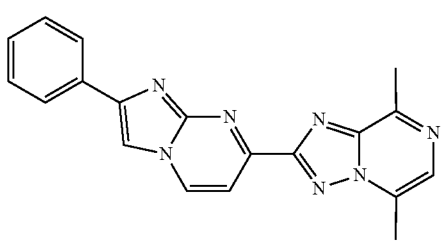 [SMILES: Cc1ncc(C)n2nc(-c3ccn4cc(-c5ccccc5)nc4n3)nc12] | 66.25 | 34.87 |
| Ex. 1 of WO2013003298 | 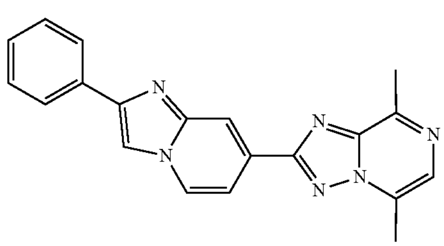 [SMILES: Cc1ncc(C)n2nc(-c3ccn4cc(-c5ccccc5)nc4c3)nc12] | 33.54 | 68.86 |

Figure 2:
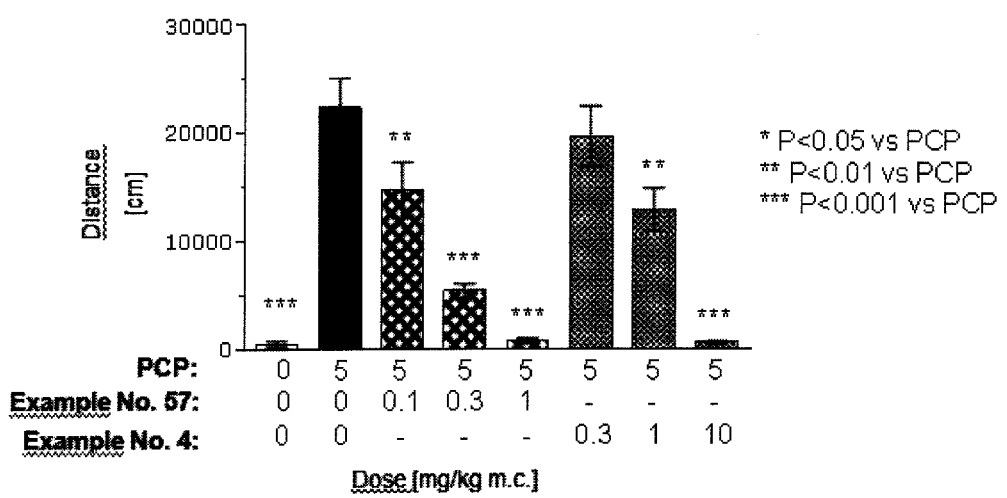

The results for selected compounds of the invention are presented in FIG. 2. The compounds of the invention were able to decrease the PCP-induced hyperlocomotion in a dose dependent manner.

The invention claimed is:

1. A compound of the general formula (I)

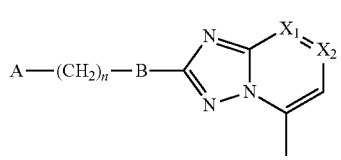
(I)

wherein:
one of $X_1$ and $X_2$ represents N, and the other one of $X_1$ and $X_2$ represents —C(CH$_3$);
A represents an unsubstituted or substituted 5-, 6- or 10-membered aryl or heteroaryl, and when substituted the substituent is selected from the group consisting of halogen, C1-C4-alkyl, CN, and —O—C1-C4-alkyl;
B is selected from the group consisting of B1 and B2 moieties:

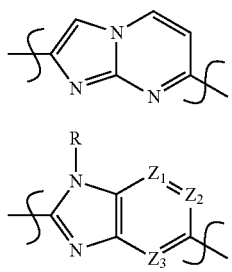

R represents H or C1-C3 alkyl;
one of $Z_1$, $Z_2$ and $Z_3$ represents —CR$^1$—, and the others of $Z_1$, $Z_2$ and $Z_3$ represent —CH—; or
one of $Z_1$, $Z_2$ and $Z_3$ represents N, one of $Z_1$, $Z_2$ and $Z_3$ represents —CH—, and one of $Z_1$, $Z_2$ and $Z_3$ represents —CR$^1$—;
R$^1$ represents H, halogen atom, CN, or heterocycloalkyl;
n is 0 or 1;
and acid addition salts thereof.

2. The compound according to claim 1, wherein n is 0.
3. The compound according to claim 1, wherein n is 1.
4. The compound according to claim 2, wherein $X_1$ represents N and $X_2$ represents —C(CH$_3$).
5. The compound according to claim 2, wherein $X_1$ represents —C(CH$_3$) and $X_2$ represents N.
6. The compound according to claim 2, wherein B represents B1 moiety.
7. The compound according to claim 2, wherein B represents B2 moiety.
8. The compound according to claim 7, wherein R represents H.
9. The compound according to claim 7, wherein R represents C1-C3 alkyl, especially CH$_3$.
10. The compound according to claim 7, wherein R$^1$ represents H.
11. The compound according to claim 7, wherein R$^1$ represents halogen atom, in particular fluorine or bromine atom.
12. The compound according to claim 7, wherein R$^1$ represents CN.
13. The compound according to claim 7, wherein R$^1$ represents heterocycloalkyl, in particular morpholinyl or pyrrolidinyl.
14. The compound according to claim 7, wherein B2 represents B21 moiety

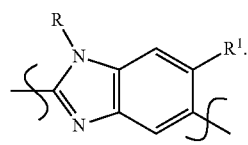

15. The compound according to claim 10, wherein B2 represents B22 moiety

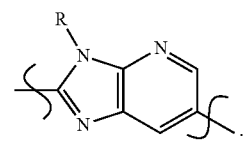

16. The compound according to claim 10, wherein B2 represents B23 moiety

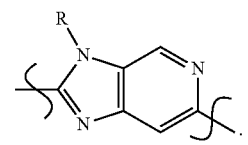

17. The compound according to claim 10, wherein B2 represents B24 moiety

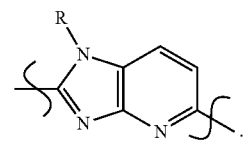

18. Pharmaceutical composition comprising as an active ingredient the compound as defined in claim 1, and pharmaceutically acceptable auxiliary substances.
19. A method of treating psychotic, neurological and cognitive functions diseases and disorders in a mammal, comprising administration to a subject in need therefor of a therapeutically effective amount of the compound as defined in claim 1.
20. The method according to claim 19, wherein the disease or disorder is selected from the group consisting of schizophrenia, delusion disorders, movement disorders, anxiety disorder, obsessive-compulsive disorder, and cognitive function disorder.
21. The compound according to claim 5 or an acid addition salt thereof, selected from the group consisting of the following:

5,8-Dimethyl-2-(2-phenylimidazo[1,2-a]pyrimidin-7-yl)
 [1,2,4]triazolo[1,5-a]pyrazine,
2-[2-(2-Methoxyphenyl)imidazo[1,2-a]pyrimidin-7-yl]-
 5,8-dimethyl[1,2,4]triazolo[1,5-a]-pyrazine,
5,8-Dimethyl-2-[2-(1,3-thiazol-2-yl)imidazo[1,2-a]pyrimidin-7-yl][1,2,4]triazolo[1,5 a]pyrazine,
5,8-Dimethyl-2-[2-(pyridin-2-yl)imidazo[1,2-a]pyrimidin-7-yl][1,2,4]triazolo[1,5 a]pyrazine,
2-[2-(5-Chlorothiophen-2-yl)imidazo[1,2-a]pyrimidin-7-yl]-5,8-dimethyl[1,2,4]triazolo[1,5 a]-pyrazine,
5,8-Dimethyl-2-[2-(thiophen-2-yl)imidazo[1,2-a]pyrimidin-7-yl][1,2,4]triazolo[1,5 a]pyrazine,
2-[2-(5-Chlorothiophen-2-yl)imidazo[1,2-a]pyrimidin-7-yl]-5,8-dimethyl[1,2,4]triazolo[1,5-a]pyrazine,
2-[2-(3-Bromophenyl)imidazo[1,2-a]pyrimidin-7-yl]-5,8-dimethyl[1,2,4]triazolo[1,5-a]pyrazine,
5,8-Dimethyl-2-[2-(3-(pyrrolidin-1-yl)phenyl)imidazo[1,2-a]pyrimidin-7-yl][1,2,4]triazolo[1,5-a]pyrazine,
2-(6-Bromo-2-phenylimidazo[1,2-a]pyrimidin-7-yl)-5,8-dimethyl[1,2,4]triazolo[1,5-a]pyrazine,
5,8-Dimethyl-2-[2-phenyl-6-(pyrrolidin-1-yl)imidazo[1,2-a]pyrimidin-7-yl][1,2,4]triazolo[1,5-a]pyrazine,
4-[7-(5,8-Dimethyl-[1,2,4]triazolo[1,5-a]pyrazin-2-yl)-2-phenylimidazo[1,2-a]pyrimidin-6-yl]morpholine,
5,8-Dimethyl-2-[6-(4-methylpiperazin-1-yl)-2-phenylimidazo[1,2-a]pyrimidin-7-yl][1,2,4]triazolo[1,5-a]pyrazine, and
7-(5,8-Dimethyl[1,2,4]triazolo[1,5-a]pyrazin-2-yl)-2-phenylimidazo[1,2-a]pyrimidino-6-carbonitrile.

22. The compound according to claim 5, wherein the compound is selected from 5,8-dimethyl-2-(2-phenylimidazo[1,2-a]pyrimidin-7-yl) [1,2,4]triazolo[1,5-a]pyrazine or an acid addition salt thereof.

\* \* \* \* \*